US008500731B2

(12) United States Patent
Byrd et al.

(10) Patent No.: US 8,500,731 B2
(45) Date of Patent: Aug. 6, 2013

(54) ADJUSTABLE LENGTH FLEXIBLE POLYMER ELECTRODE CATHETER AND METHOD FOR ABLATION

(75) Inventors: Israel A. Byrd, Richfield, MN (US);
Saurav Paul, Minnetonka, MN (US);
Claire T. Edlebeck, Duluth, MN (US);
Riki C. Thao, Brooklyn Park, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1060 days.

(21) Appl. No.: 12/347,097

(22) Filed: Dec. 31, 2008

(65) Prior Publication Data

US 2009/0171349 A1    Jul. 2, 2009

Related U.S. Application Data

(63) Continuation-in-part of application No. 11/963,430, filed on Dec. 21, 2007, now Pat. No. 8,118,809.

(51) Int. Cl.
*A61B 18/18* (2006.01)

(52) U.S. Cl.
USPC .......................................... 606/41

(58) Field of Classification Search
USPC .................. 606/32–50; 607/101–105
See application file for complete search history.

(56) References Cited

U.S. PATENT DOCUMENTS

| | | |
|---|---|---|
| 4,911,174 A | 3/1990 | Pederson |
| 4,945,912 A | 8/1990 | Langberg |
| 5,122,137 A | 6/1992 | Lennox |
| 5,246,438 A | 9/1993 | Lanberg |
| 5,341,807 A | 8/1994 | Nardella |
| 5,372,603 A | 12/1994 | Acker et al. |
| 5,382,247 A | 1/1995 | Cimino et al. |
| 5,433,708 A | 7/1995 | Nichols |
| 5,447,529 A | 9/1995 | Marchlinski |
| 5,472,441 A | 12/1995 | Edwards et al. |
| 5,542,928 A | 8/1996 | Evans |
| 5,545,161 A | 8/1996 | Imran |
| 5,582,609 A | 12/1996 | Swanson et al. |
| 5,697,925 A | 12/1997 | Taylor |
| 5,836,990 A | 11/1998 | Li |
| 5,868,737 A | 2/1999 | Taylor et al. |

(Continued)

FOREIGN PATENT DOCUMENTS

WO   WO2005039835   5/2005

OTHER PUBLICATIONS

PCT International Search Report and Written Opinion of the International Searching Authority for PCT/US06/42119 dated Sep. 13, 2007.

*Primary Examiner* — Laura A Bouchelle
*Assistant Examiner* — Diva K Chander
(74) *Attorney, Agent, or Firm* — Wiley Rein LLP

(57) ABSTRACT

An ablation catheter includes a flexible elongated shaft having a flexible electrode at its distal end. The flexible electrode includes an inner, flexible, electrically-conductive element and an outer, flexible, electrically-conductive polymer layer in electrical contact with the inner, flexible, electrically-conductive element. The catheter further includes an electrically insulative sheath surrounding at least a portion of the flexible electrode and a linear displacement mechanism capable of adjusting at least one of the electrically insulative sheath and the flexible electrode to vary a length of the flexible electrode exposed at the distal end of the shaft. Also disclosed is an adjustable length ablation electrode and methods of ablating tissue.

25 Claims, 19 Drawing Sheets

U.S. PATENT DOCUMENTS

| | | |
|---|---|---|
| 5,910,129 A | 6/1999 | Koblish et al. |
| 5,938,694 A | 8/1999 | Jaraczewski et al. |
| 6,013,074 A | 1/2000 | Taylor |
| 6,039,731 A | 3/2000 | Taylor et al. |
| 6,048,329 A | 4/2000 | Thompson et al. |
| 6,066,139 A | 5/2000 | Ryan et al. |
| 6,071,274 A | 6/2000 | Thompson et al. |
| 6,071,279 A | 6/2000 | Thompson et al. |
| 6,076,012 A | 6/2000 | Swanson et al. |
| 6,113,592 A | 9/2000 | Taylor |
| 6,113,593 A | 9/2000 | Tu et al. |
| 6,171,304 B1 | 1/2001 | Netherly et al. |
| 6,210,406 B1 | 4/2001 | Webster |
| 6,217,573 B1 | 4/2001 | Webster |
| 6,217,574 B1 | 4/2001 | Webster |
| 6,241,754 B1 | 6/2001 | Swanson et al. |
| 6,246,898 B1 | 6/2001 | Vesely et al. |
| 6,264,653 B1 | 7/2001 | Falwell |
| 6,291,568 B1 | 9/2001 | Lussey et al. |
| 6,304,776 B1 | 10/2001 | Montermann |
| 6,322,558 B1 | 11/2001 | Taylor et al. |
| 6,325,799 B1 | 12/2001 | Goble |
| 6,330,473 B1 | 12/2001 | Swanson et al. |
| 6,391,024 B1 | 5/2002 | Sun et al. |
| 6,402,746 B1 | 6/2002 | Whayne et al. |
| 6,423,057 B1 | 7/2002 | He et al. |
| 6,454,758 B1 | 9/2002 | Thompson et al. |
| 6,495,069 B1 | 12/2002 | Lussey et al. |
| 6,616,657 B2 | 9/2003 | Simpson et al. |
| 6,638,222 B2 | 10/2003 | Chandrasekaran et al. |
| 6,646,540 B1 | 11/2003 | Lussey |
| 6,673,068 B1 * | 1/2004 | Berube .............. 606/33 |
| 6,696,844 B2 | 2/2004 | Wong et al. |
| 6,730,082 B2 | 5/2004 | Messing et al. |
| 6,845,264 B1 | 1/2005 | Skladnev et al. |
| 6,882,885 B2 | 4/2005 | Levy, Jr. et al. |
| 6,936,047 B2 | 8/2005 | Nasab et al. |
| 6,974,457 B2 | 12/2005 | Gibson |
| 6,999,821 B2 | 2/2006 | Jenney et al. |
| 7,226,446 B1 * | 6/2007 | Mody et al. .............. 606/33 |
| 7,311,704 B2 | 12/2007 | Paul |
| 7,326,204 B2 | 2/2008 | Paul et al. |
| 7,326,205 B2 | 2/2008 | Paul et al. |
| 7,326,206 B2 | 2/2008 | Paul et al. |
| 7,794,402 B2 * | 9/2010 | Wang .............. 600/459 |
| 2002/0123749 A1 | 9/2002 | Jain |
| 2003/0055415 A1 * | 3/2003 | Yu et al. .............. 606/21 |
| 2003/0093069 A1 * | 5/2003 | Panescu et al. .............. 606/34 |
| 2005/0234437 A1 * | 10/2005 | Baxter et al. .............. 606/15 |
| 2006/0258978 A1 * | 11/2006 | Vanney .............. 604/95.01 |
| 2007/0055230 A1 * | 3/2007 | Chee et al. .............. 606/41 |
| 2007/0112342 A1 * | 5/2007 | Pearson et al. .............. 606/34 |
| 2007/0203480 A1 * | 8/2007 | Mody et al. .............. 606/33 |
| 2008/0161889 A1 | 7/2008 | Paul et al. |

\* cited by examiner

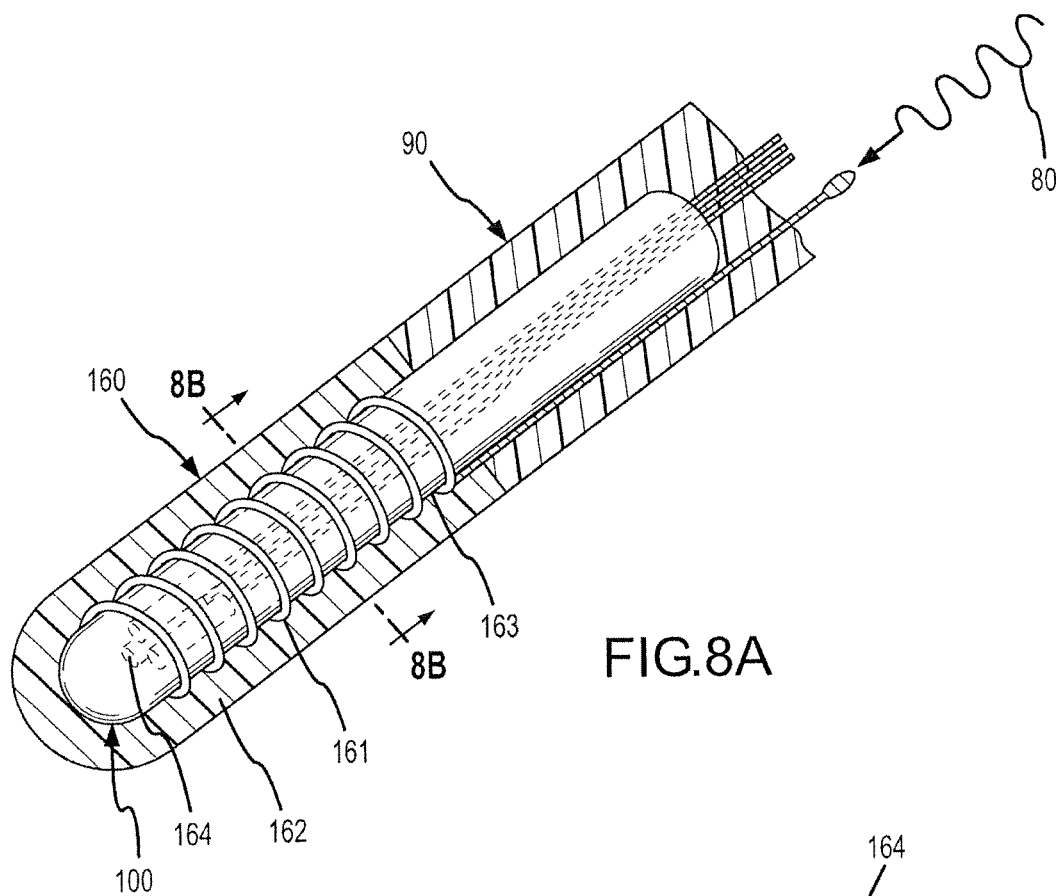
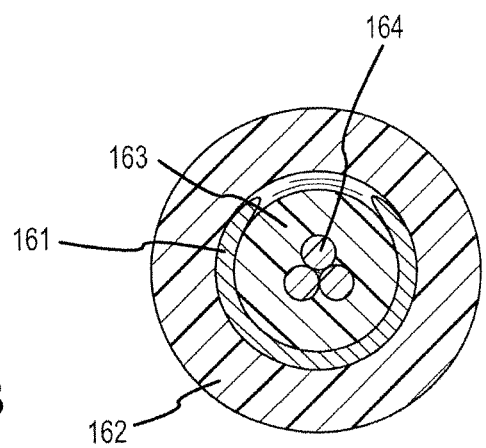

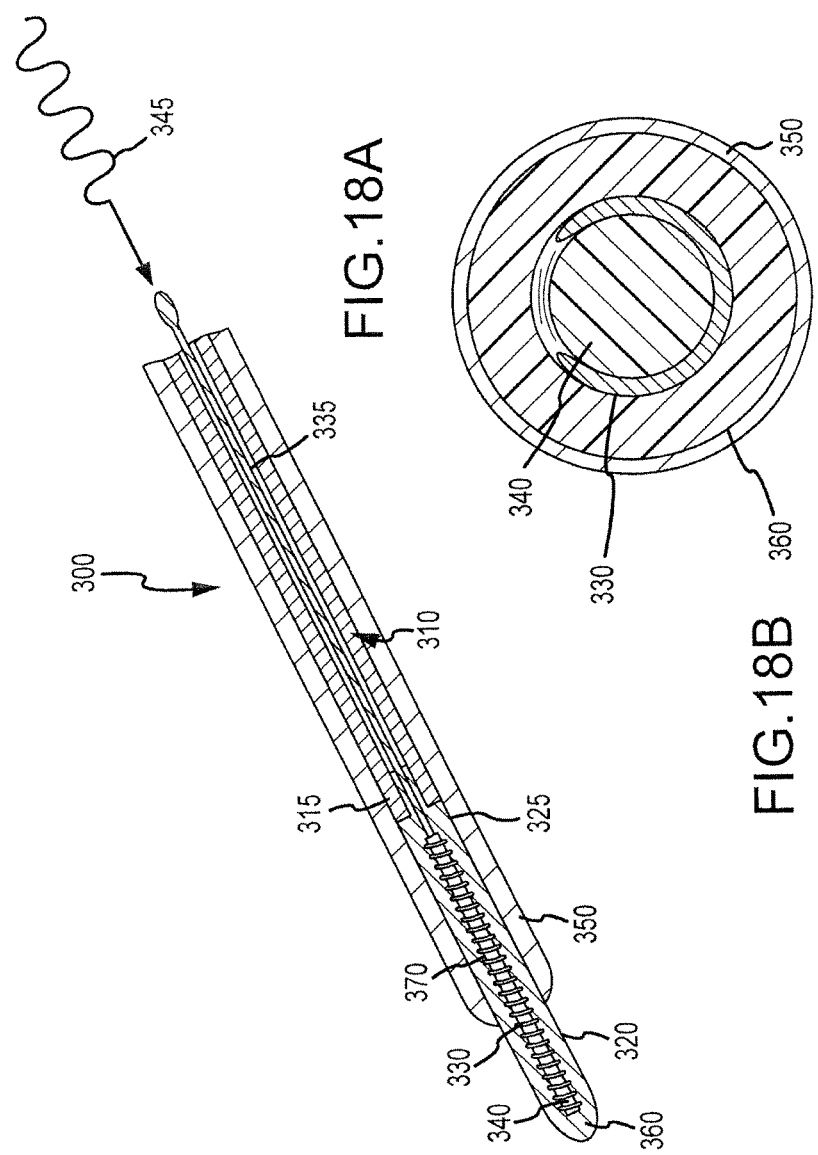

ADJUSTABLE LENGTH FLEXIBLE POLYMER ELECTRODE CATHETER AND METHOD FOR ABLATION

CROSS-REFERENCE TO RELATED APPLICATIONS

This application is a continuation-in-part of U.S. application Ser. No. 11/963,430, filed Dec. 21, 2007, now pending ("the '430 application"), which is related to U.S. application Ser. No. 11/963,321, filed Dec. 21, 2007 ("the '321 application"). The '430 application and the '321 application are hereby incorporated by reference in their entirety as though fully set forth herein.

BACKGROUND OF THE INVENTION a. Field of the Invention

The present invention pertains generally to an electrophysiological device and method for providing energy to biological tissue and, more particularly, to an ablation apparatus with an adjustable length flexible polymer electrode.

b. Background Art

Ablation devices, including radiofrequency ("RF") ablation devices, have heretofore been provided. Many medical procedures, including for example, those related to creating tissue lesions with electrical energy, rely on an ability to adapt the medical procedure to specific patient physiological characteristics. Depending upon the specific characteristics of the region targeted during the procedures, the ability to modify the type and size of the lesions created in a single treatment setting is increasingly important. In RF ablation devices, the type of lesion created, for example a spot lesion or a linear lesion, and the size of the lesion, are often limited by the size of the ablation electrode. This gives rise to functional and theoretical challenges associated with conventional devices.

There is a need for improved ablation devices that provide an ability to control the type and size of ablation lesions during a medical procedure.

There is also a need for improved ablation devices using flexible polymer electrodes that provide an ability to control the type and size of lesions during RF ablation treatments.

There is also a need for improved ablation devices having means to controllably alter the length of the flexible polymer ablation electrode during RF ablation treatments.

BRIEF SUMMARY OF THE INVENTION

The present invention provides for ablation devices and methods having an adjustable length flexible polymer ablation electrode.

An objective of the present invention is to provide an adjustable length flexible conductive polymer electrode that may be used for RF ablation treatment.

Another object of the present invention is to provide an adjustable length, flexible, conductive polymer-based electrode for RF ablation, which can be used in a wide variety of tissue environments.

Yet another object of the present invention is to provide an adjustable length, flexible, conductive polymer-based electrode for RF ablation, which can be used to vary the type and size of ablation lesions created in a single treatment setting based on a patient's physiological characteristics.

Still another object of the invention is to provide an ablation device with a linear displacement mechanism that can vary the length of a flexible conductive polymer electrode during a medical procedure.

Yet another object of the present invention is to provide a method of ablation using a device having an adjustable length flexible conductive polymer electrode.

Disclosed herein is an adjustable length flexible polymer electrode for ablation therapy. In one embodiment, an ablation catheter includes a flexible elongated shaft and a flexible electrode coupled to a distal end of the flexible elongated shaft. The flexible electrode includes an inner, flexible, electrically-conductive element and an outer, flexible, electrically-conductive polymer layer in electrical contact with the inner, flexible, electrically-conductive element. The ablation catheter further includes an electrically insulative sheath surrounding at least a portion of the flexible electrode and a linear displacement mechanism capable of adjusting at least one of the electrically insulative sheath and the flexible electrode to vary a length of the flexible electrode exposed at the distal end of the flexible elongated shaft.

In one aspect, the length of the flexible electrode exposed at the distal end of the flexible elongated shaft varies from about 0.1 mm to about 100 mm. In another aspect, the length of the flexible electrode exposed at the distal end of the flexible elongated shaft varies from about 0.5 mm to about 25 mm. The linear displacement mechanism may include a push-pull pulley, a screw drive mechanism, or a rack and pinion mechanism.

The inner electrically conductive element may be a helical coil, and the helical coil may surround a flexible, electrically insulative member. The ablation catheter may optionally include a seal between the electrically insulative sheath and the flexible shaft.

In another embodiment of the invention, an adjustable length ablation electrode includes an inner, flexible, electrically-conductive element and an outer, flexible, electrically-conductive polymer layer in electrical contact with the inner, flexible, electrically-conductive element. The electrode further includes an electrically insulative sheath surrounding at least a portion of the outer, flexible, electrically-conductive polymer layer. The electrically insulative sheath is movable from a first position to a second position to expose a first length of the ablation electrode in the first position and a second length of the ablation electrode in the second position, the second length being greater than the first length. In one aspect, the first length and the second length may each be between about 0.1 mm and about 100 mm. In another aspect, the first length is about 5 mm or less and the second length is between about 5 mm and about 100 mm.

The adjustable length ablation electrode may further include a linear displacement mechanism for moving the electrically insulative sheath between the first position and the second position. The linear displacement mechanism may include a push-pull pulley, a screw drive mechanism or a rack and pinion mechanism.

The inner electrically conductive element may be a helical coil, and the helical coil may surround a flexible, electrically insulative member. The electrode may optionally include a seal between the electrically insulative sheath and the outer electrically conductive polymer layer.

In another embodiment of the invention an ablation electrode includes a flexible, elongated shaft and a flexible electrode coupled to a distal end of the flexible, elongated shaft. The flexible electrode includes an inner, flexible, electrically conductive element and an outer, flexible, electrically conductive polymer layer in electrical contact with the inner, flexible, electrically-conductive element. The ablation catheter further includes an electrically insulative sheath surrounding at least a portion of the flexible electrode. The flexible electrode and the electrically insulative sheath are movable with respect to each other to expose more or less of a length of the flexible electrode. In one aspect, the exposed length of the flexible electrode may be between about 0.1 mm and about 100 mm. In another aspect, the exposed length of the flexible electrode is between about 0.5 mm and about 25 mm.

The ablation catheter may further include a linear displacement mechanism adapted to move the flexible electrode and the electrically insulative sheath with respect to each other. The linear displacement mechanism may include a push-pull pulley, a screw drive mechanism or a rack and pinion mechanism.

The inner electrically conductive element may be a helical coil, and the helical coil may surround a flexible, electrically insulative member. The ablation catheter may optionally include a seal between the electrically insulative sheath and the flexible electrode.

A method for ablating tissue includes the steps of providing an ablation catheter having a flexible elongated shaft; a flexible electrode coupled to a distal end of the flexible elongated shaft, the flexible electrode comprising an inner, flexible, electrically conductive element and an outer, flexible, electrically conductive polymer layer in electrical contact with the inner, flexible, electrically conductive element; and an electrically insulative sheath surrounding at least a portion of the flexible electrode. The method further includes placing the exposed portion of the flexible electrode against tissue to be ablated and energizing the electrode to create a first lesion having a first length. At least one of the flexible electrode and the electrically insulative sheath are adjusted to increase or decrease the length of the exposed portion of the flexible electrode and the flexible electrode is energized to create a second lesion having a second length. In one aspect, the first length and the second length may be between about 0.1 mm and about 100 mm. In another aspect, the first length and the second length may be between about 0.5 mm and about 25 mm. The tissue may be an epicardial tissue.

The adjusting step may optionally include actuating a linear displacement mechanism to adjust at least one of the electrically insulative sheath and the flexible electrode. In this aspect, the linear displacement mechanism may include at least one of a push-pull pulley, a screw drive mechanism, and a rack and pinion mechanism.

An advantage of using an adjustable length flexible conductive polymer electrode is the improved ability to vary the type and size of ablation lesions created in a single treatment setting.

Another advantage of using an adjustable length, flexible conductive polymer electrode in an ablation device is increased speed and efficacy of ablation procedures.

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 8A and 8B are cross-sectional views of yet another preferred embodiment of the invention with thermal sensing.

FIGS. 18A and 18B are cross-sectional views of another preferred embodiment in which the catheter includes an adjustable-length flexible polymer electrode.

DETAILED DESCRIPTION OF THE INVENTION

Figure 1A:
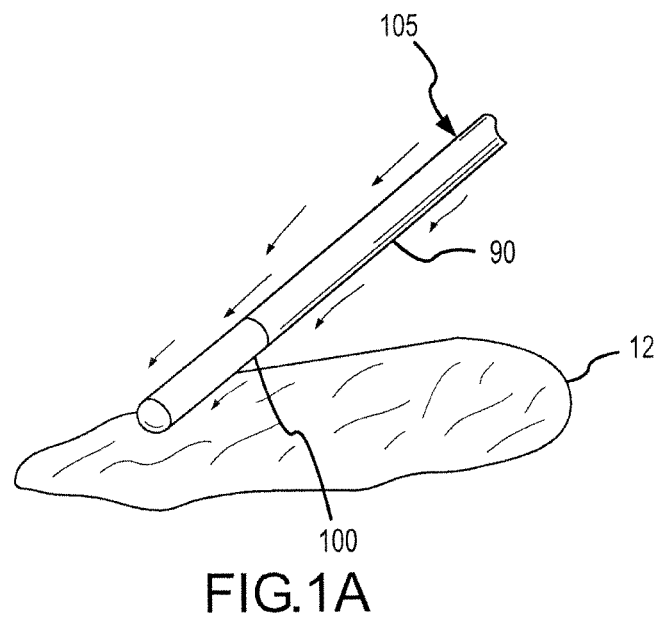
FIGS. 1A and 1B are perspective views of a sample embodiment of the present invention, illustrating how the present invention may be used to ablate tissue.

A flexible conductive polymer electrode for ablation is disclosed, along with methods for using and methods of manufacturing the flexible conductive polymer electrode. Also disclosed is an adjustable length flexible conductive polymer electrode. Of course, it is within the spirit and scope of the present invention to use the flexible conductive polymer electrode for other applications, including, but not limited to, electrophysiology studies such as mapping and diagnosis.

As used herein, the term "conductive polymer" refers to a polymer that is formed using at least some conductive materials and which is conductive even in its quiescent state such that the polymer may conduct sufficient energy to ablate tissue. The present invention will work with various conductive polymer materials. For example, U.S. Pat. No. 6,999,821, which is hereby incorporated by reference as though fully set forth herein, discloses intrinsically conductive and conductor-filled polymers that may be useful in the present invention. As disclosed therein, intrinsically conductive polymers include polyacetylene, polypyrrole, and polyanaline, among others. Conductor-filled polymers may include presently available materials approved for implantation such as silicone rubber with embedded metallic, carbon or graphite particles or powder. Silver filled silicone rubbers of the kind manufactured by NuSil or Specialty Silicone Products, modified so as to be approved for implantation, are of potential utility. An example is silver-coated, nickel-filled silicone rubber sold as NuSil R2637.

The substrate need not be silicone; for example, it is contemplated that other insulating or weakly conductive materials (e.g., non-conductive elastomers) may be embedded with conductive materials, conductive alloys, and/or reduced metal oxides (e.g., using one or more of gold, silver, platinum, iridium, titanium, tantalum, zirconium, vanadium, niobium, hafnium, aluminum, silicone, tin, chromium, molybdenum, tungsten, lead, manganese, beryllium, iron, cobalt, nickel, palladium, osmium, rhenium, technetium, rhodium, ruthenium, cadmium, copper, zinc, germanium, arsenic, antimony, bismuth, boron, scandium, and metals of the lanthanide and actinide series, and, if appropriate, at least one electroconductive agent). The conductive material may be in the form of powder, grains, fibers, or other shaped forms. The oxides can be mixtures comprising sintered powders of an oxycompound. The alloy may be conventional, for example titanium boride.

Other examples of conductive polymers that may be used in the present invention include the conductive polymers described and disclosed in U.S. Pat. Nos. 6,646,540, 6,495,069, and 6,291,568, all of which are incorporated by reference as if set forth in their entireties herein.

The conductive polymer may be pressure sensitive, in that the electrical resistance of the electrode may vary inversely in proportion to the pressure that is applied thereto. It should be understood, however, that the flexible conductive polymer electrodes disclosed herein are conductive even in their quiescent state (that is, when not under stress), and are therefore distinguished from the pressure sensitive conductive composite ("PSCC") electrodes disclosed in U.S. application Ser. No. 11/647,316, filed 29 Dec. 2007, which are non-conductive in their quiescent state. Preferably, the conductive polymer material will also meet cytotoxity, hemolysis, systemic toxicity and intracutaneous injection standards.

Figure 1B:
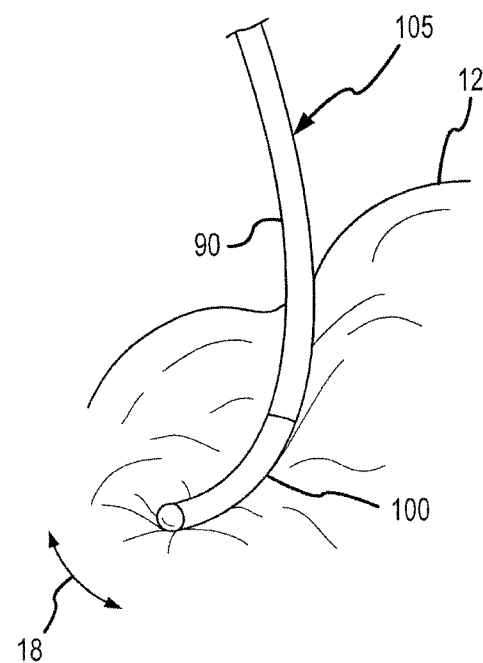

FIGS. 1A and 1B illustrate a sample embodiment of the present invention. As illustrated in FIGS. 1A and 1B, a flexible conductive polymer electrode 105 generally includes a catheter shaft 90 and a contact surface 100 that extends from catheter shaft 90. Electrode 105 is flexible such that when it comes into contact with tissue 12, electrode 105 is deflected in direction 18 as illustrated in FIG. 1B, thereby increasing the contact surface between electrode 105 and tissue 12. Advantageously, this increased contact surface improves the efficacy of, for example, the delivery of ablating energy to the tissue. One of skill in the art will recognize that increasing the force on electrode 105 will tend to increase the contact between electrode 105 and tissue 12, as tissue 12 will tend to "wrap around" electrode 105.

Figure 2:
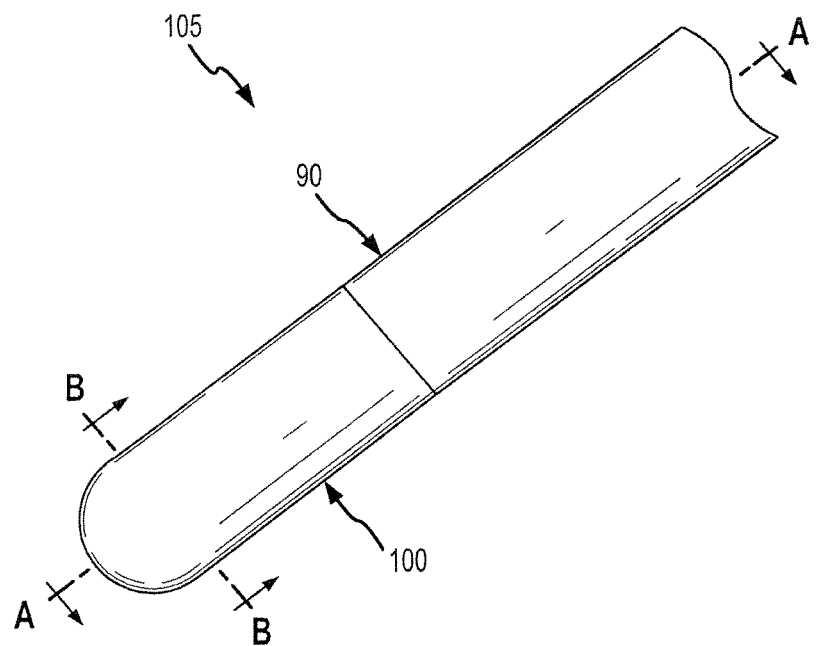
FIG. 2 is a side view drawing of an exemplary catheter having a flexible conductive polymer electrode.

FIG. 2 is a close-up of the sample embodiment depicted in FIGS. 1A and 1B. FIG. 2 illustrates cross-sectional reference lines A-A and B-B, which will be used to illustrate preferred embodiments of the present invention.

Figure 3A:
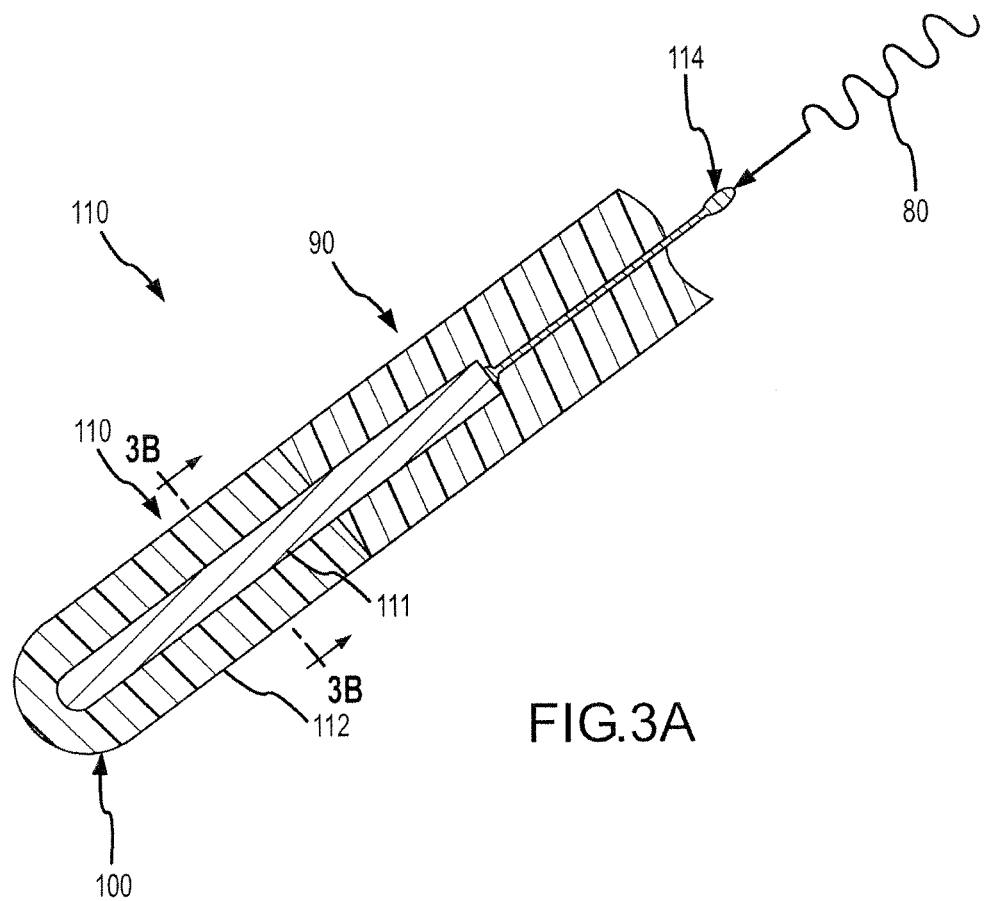
FIGS. 3A and 3B are cross-sectional views of a preferred embodiment of a catheter having a flexible conductive polymer electrode.
Figure 3B:
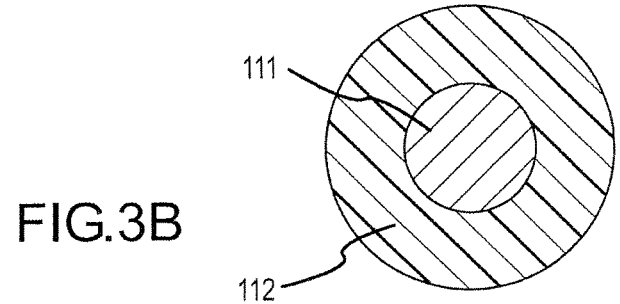

FIGS. 3A and 3B illustrate a preferred embodiment of the present invention, revealing two cross sectional drawings taken along the reference lines of A-A and B-B as labeled in FIG. 2. In this preferred embodiment, the electrode 110 includes catheter shaft 90 and a contact surface 100 that extends from catheter shaft 90. Catheter shaft 90 may be either conductive or non-conductive, and preferably, catheter shaft 90 is non-conductive. In this embodiment, the flexible conductive polymer forms the working surface of the electrode that is used for ablation therapy. As depicted in FIGS. 3A and 3B, electrode 110 includes a flexible inner conductive core 111 and an outer conductive polymer substrate layer 112, which is mechanically and electrically coupled to the flexible inner conductive core 111. Flexible inner conductive core 111 may include a flat top (like the top of a right cylinder), or optionally it may include a portion of a sphere on its distal end as illustrated in FIG. 3A. Flexible inner conductive core 111 may be connected to an electrical conductor 114, which may be connected to an RF generator (e.g., RF current source 80). In use, in this preferred embodiment, the electrode 110 ablates tissue by delivering ablation energy through the inner conductive core 111.

Figure 4A:
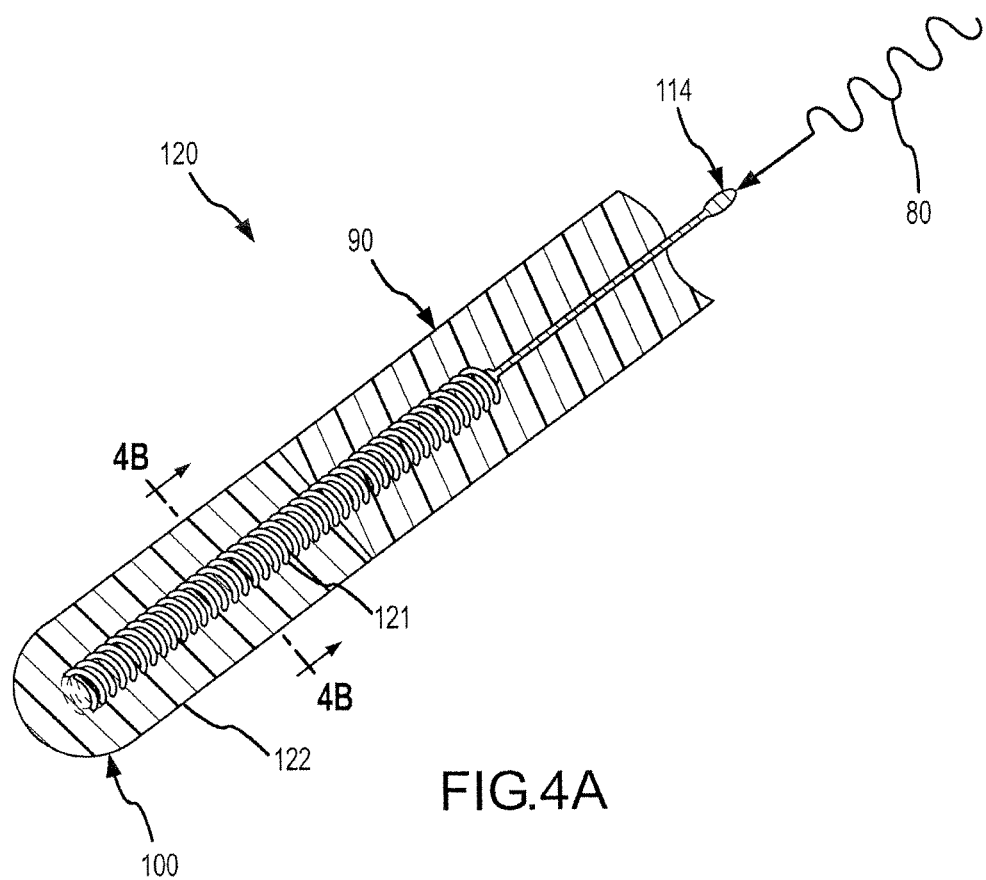
FIGS. 4A and 4B are cross-sectional views of another preferred embodiment in which the electrode is in the shape of a helix.
Figure 4B:
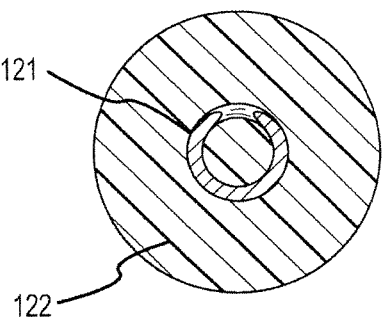

FIGS. 4A and 4B illustrate another preferred embodiment of the present invention, revealing two cross sectional drawings taken along the reference lines of A-A and B-B as labeled in FIG. 2. Electrode 120 extends from a catheter shaft 90 and generally includes flexible inner conductive coil 121 in the shape of a helix and a flexible conductive polymer substrate layer 122 within which the inner conductive coil 121 is located. Flexible inner conductive coil 121 is connected to an electrical conductor 114, which may be connected to an RF generator (e.g., RF current source 80). In use, in this preferred embodiment, the electrode 120 ablates tissue by delivering ablation energy through inner conductive coil 121. Preferably, the reference electrode is connected to an electrical ground.

Figure 5A:
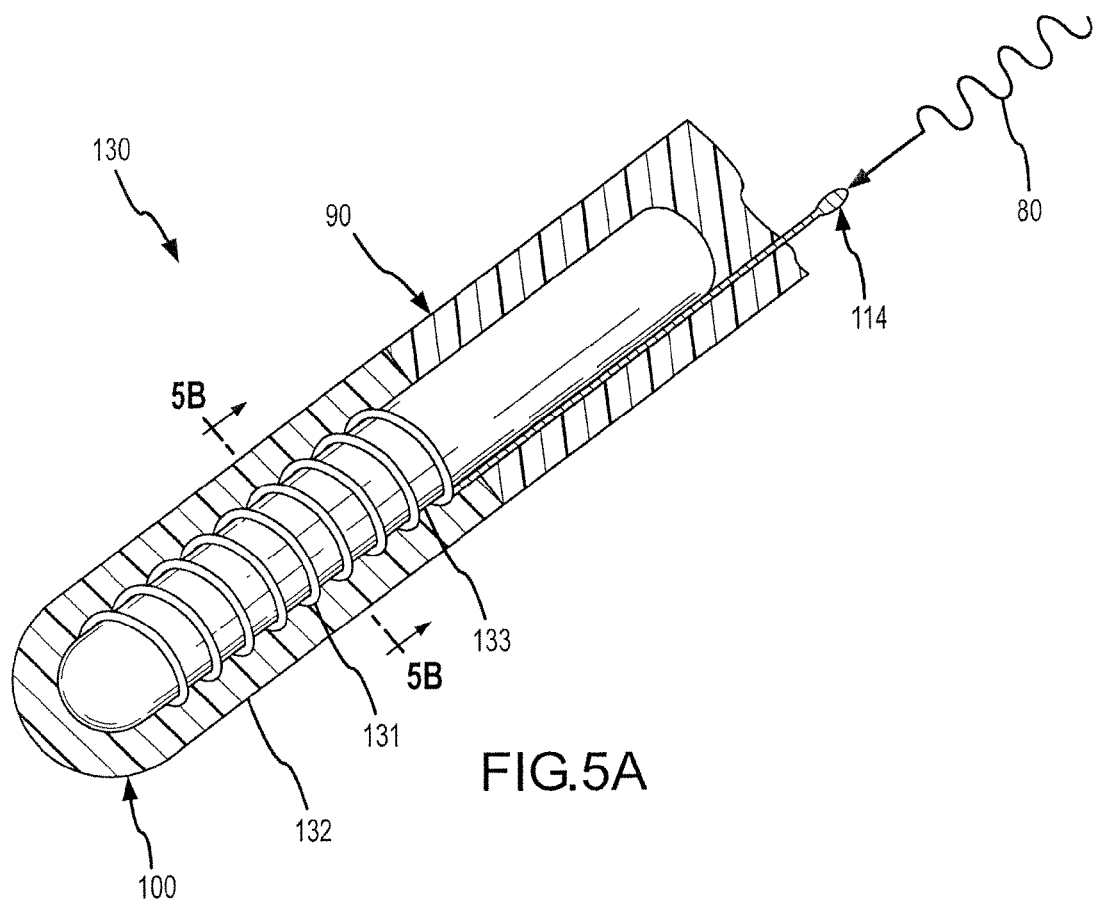
FIGS. 5A and 5B are cross-sectional views of another preferred embodiment in which the electrode is located about a flexible inner core.
Figure 5B:
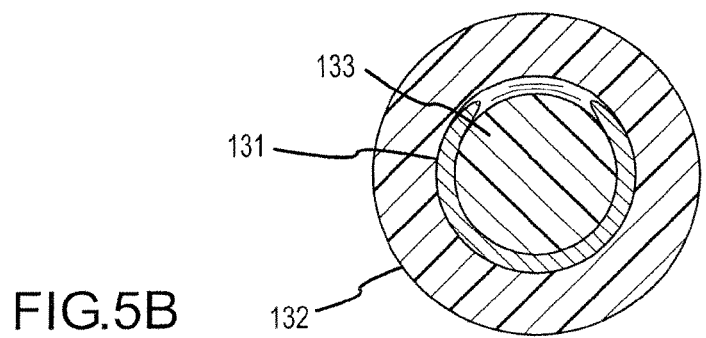

FIGS. 5A and 5B illustrate yet another preferred embodiment of the present invention, revealing two cross sectional drawings taken along the reference lines of A-A and B-B as labeled in FIG. 2. Electrode 130 extends from a catheter shaft 90 and generally includes: flexible inner conductive coil 131 in the shape of a helix; an outer flexible conductive polymer substrate layer 132; and a flexible shaft 133 located within the helix of the flexible inner conductive coil 131.

Flexible shaft 133 is preferably an electrically insulative shaft, but may be electrically conductive without departing from the spirit and scope of the present invention. Moreover, flexible shaft 133 is preferably thermally conductive, as described in further detail below. Flexible shaft 133 may optionally include a portion of a sphere on its distal end as shown in FIG. 5A.

Flexible inner conductive coil 131 is connected to an electrical conductor 114, which may be connected to an RF generator (e.g., RF current source 80). In use, in this preferred embodiment the electrode 130 ablates tissue by delivering energy through the inner conductive coil 131. Preferably, the reference electrode is connected to an electrical ground.

Figure 6A:
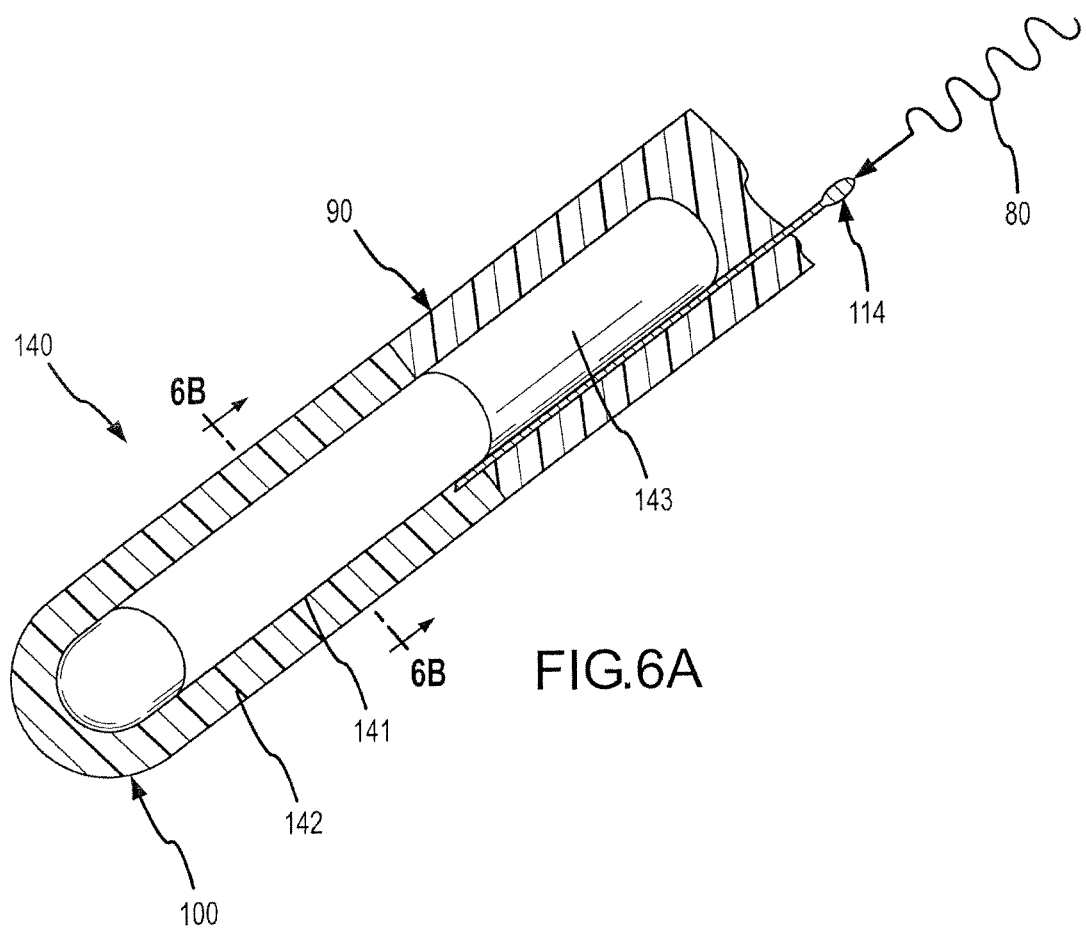
FIGS. 6A and 6B are cross-sectional views of another preferred embodiment in which the electrode is in the shape of a mesh.
Figure 6B:
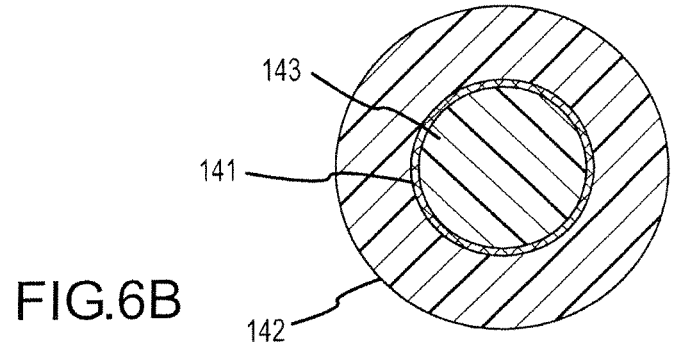

FIGS. 6A and 6B illustrate yet another preferred embodiment of the present invention, revealing two cross sectional drawings taken along the reference lines of A-A and B-B as labeled in FIG. 2. Electrode 140 extends from a catheter shaft 90 and generally includes: flexible inner conductive sheath 141 formed of a mesh; an outer flexible conductive polymer substrate layer 142; and a flexible shaft 143, which is preferably electrically insulative, located interiorly of the flexible inner conductive sheath 141. Flexible shaft 143 may optionally include a portion of a sphere at its distal end as shown in FIG. 6A. Flexible sheath 141 is connected to an electrical conductor 114, which may be connected to an RF generator (e.g., RF current source 80). In use, in this preferred embodiment, the electrode 140 ablates tissue by delivering energy through the flexible sheath 141. Preferably, the reference electrode is connected to an electrical ground.

Figure 7A:
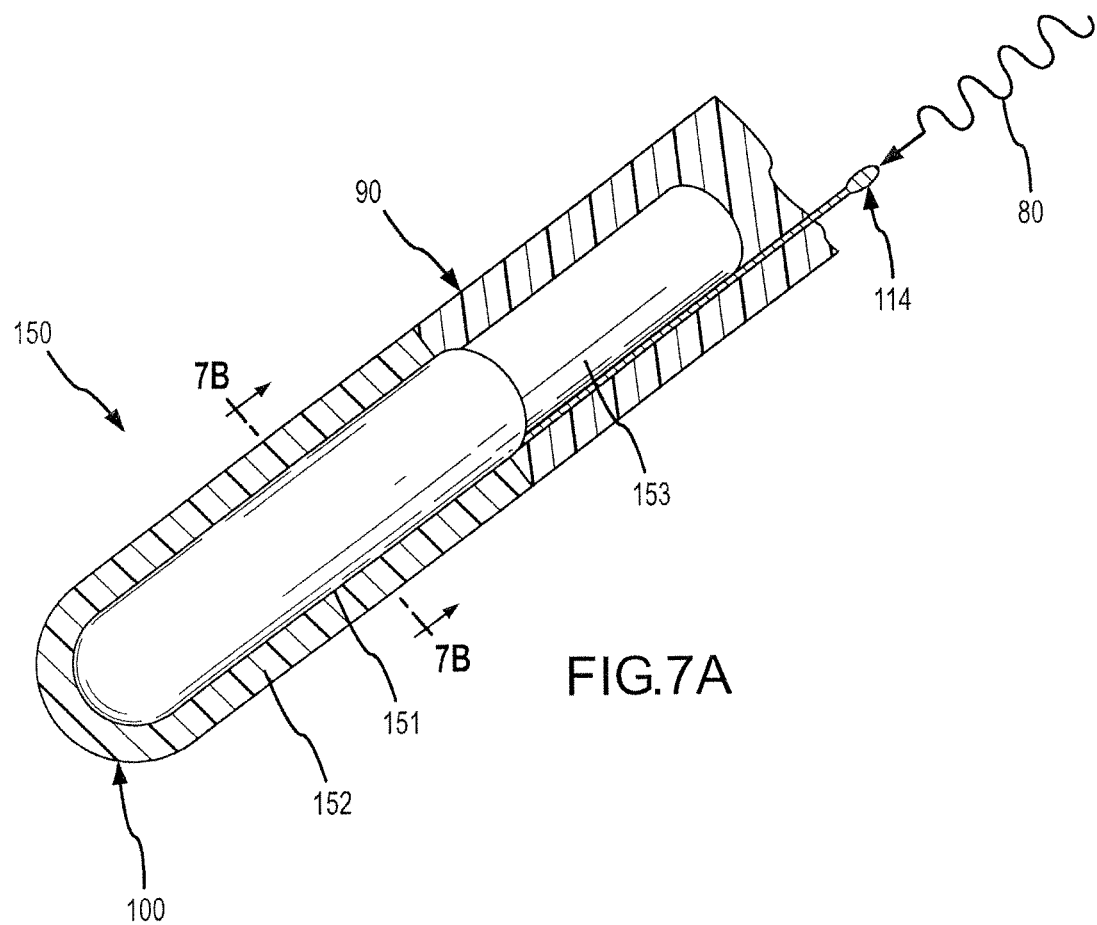
FIGS. 7A and 7B are cross-sectional views of another preferred embodiment in which the flexible conductive polymer electrode is formed as an outer substrate layer.
Figure 7B:
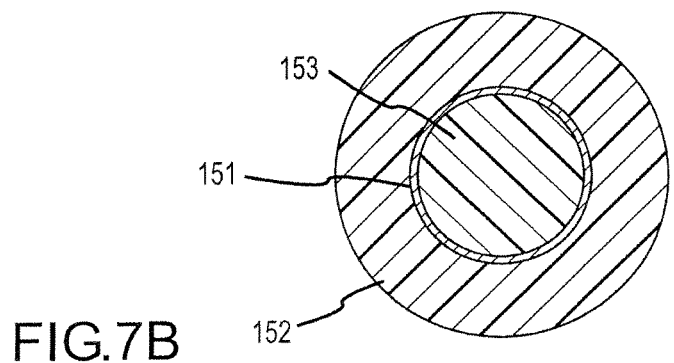

FIGS. 7A and 7B illustrate yet another preferred embodiment of the present invention, revealing two cross sectional drawings taken along the reference lines of A-A and B-B as labeled in FIG. 2. Electrode 150 extends from a catheter shaft 90 and generally includes: an electrically insulative flexible shaft 153; a flexible inner conductive layer 151 (formed, for example, as a coating and/or wrap around flexible shaft 153); and an outer flexible conductive polymer substrate layer 152. Electrically insulative flexible shaft 153 and flexible inner conductive layer 151 may optionally include a portion of a sphere at their respective distal ends (as illustrated in FIG. 7A). Flexible inner conductive core 151 is connected to an electrical conductor 114, which may be connected to an RF generator (e.g., RF current source 80). In use, in this preferred embodiment the electrode 150 ablates tissue by delivering ablation energy through the flexible inner conductive core 151. Preferably, the reference electrode is connected to an electrical ground.

FIGS. 8A and 8B illustrate yet another preferred embodiment of the present invention, revealing two cross sectional drawings taken along the reference lines of A-A and B-B as labeled in FIG. 2. Electrode 160 extends from a catheter shaft 90 and generally includes a thermally conductive, electrically insulative, flexible shaft 163; a flexible inner conductive layer 161 (formed, for example, as a coating and/or wrap around flexible shaft 163, or as illustrated in FIG. 8, a helix); an outer flexible conductive polymer substrate layer 162; and a plurality of thermal sensors 164 located within the thermally conductive, electrically insulative, flexible shaft 163 to measure temperatures at various locations therein. Electrically insulative flexible shaft 163 and flexible inner conductive layer 161 may optionally include a portion of a sphere at their respective distal ends (as illustrated in FIG. 8A). Flexible inner conductive coil 161 is connected to an electrical conductor 114, which may be connected to an RF generator (e.g., RF current source 80). In use, in this preferred embodiment, the electrode 160 ablates tissue by delivering ablation energy through the flexible inner conductive coil 161. Preferably, the reference electrode is connected to an electrical ground.

As one of ordinary skill can appreciate, temperature sensors 164 (such as thermistors, thermocouples or other temperature sensors) can be used to monitor operation temperature to help ensure effective and safe ablation treatment. For example, one or more temperatures may be used at a variety of locations, including, for example, at a distal end of the device to monitor a temperature that is at least in part reflective of the tissue temperature, or even within the electrically insulative shaft. Other potential locations include the use of a temperature sensor located at a location where a cooling fluid enters or exits the device. Of course, temperature sensors may be located at additional or different locations.

Figure 9A:
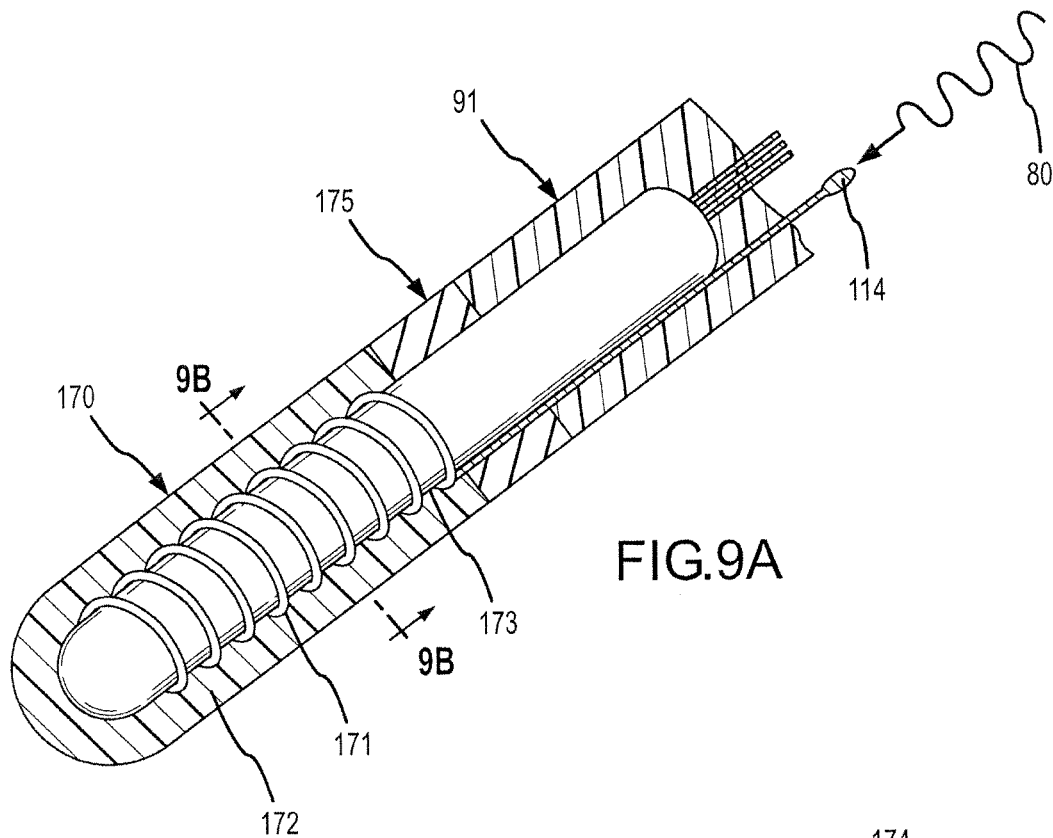
FIGS. 9A and 9B are cross-sectional views of another preferred embodiment in which the electrode is adjacent a heat sink.
Figure 9B:
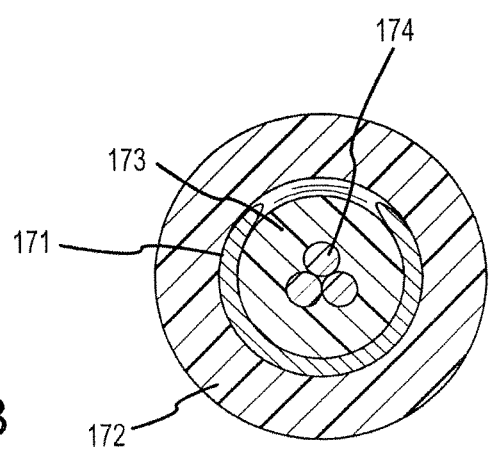

FIGS. 9A and 9B illustrate yet another preferred embodiment of the present invention, revealing two cross sectional drawings taken along the reference lines of A-A and B-B as labeled in FIG. 2. Electrode 170 extends from a catheter shaft 90 and generally includes: a thermally conductive, electrically insulative, flexible shaft 173; a flexible inner conductive layer 171 (formed, for example, as a coating and/or wrap around flexible shaft 173, or as illustrated in FIG. 9, a helix); an outer flexible conductive polymer substrate layer 172; a heat sink 175 thermally coupled to flexible shaft 173; and a plurality of thermal sensors 174 located within the thermally conductive, electrically insulative, flexible shaft 173 to measure temperatures at various locations therein. Electrically insulative flexible shaft 173 and flexible inner conductive layer 171 may optionally include a portion of a sphere at their respective distal ends (as illustrated in FIG. 9A). Flexible inner conductive coil 171 is connected to an electrical conductor 114, which may be connected to an RF generator (e.g., RF current source 80). In use, in this preferred embodiment, the electrode 170 ablates tissue by delivering ablation energy through the flexible inner conductive coil 171. Preferably, the reference electrode is connected to an electrical ground.

As one of ordinary skill can appreciate, temperature sensors 174 (such as thermistors, thermocouples or other temperature sensors) can be used to monitor operation temperature to help ensure effective and safe ablation treatment. Heat sink 175 helps to prevent the electrode from overheating the electrode and the tissue.

Electrical conductor 114 may be implemented using a single conductive wire or multiple strands of wire. Preferably, the wires are made of flexible conductive materials which allow the surface contacting area of the electrode to be bent and formed into various shapes to provide better contact with the tissue (e.g., an increased contact area between the electrode and the tissue). Acceptable materials include, but are not limited to, stainless steel, nickel titanium (e.g., Nitinol), tantalum, copper, platinum, iridium, gold, or silver, and combinations thereof. Preferably, the material used to manufacture the conductive element is a bio-compatible electrically conductive material, such as platinum, gold, silver, nickel titanium, and combinations thereof. Other electrically conductive materials coated with bio-compatible materials may also be employed, including for example, gold-plated copper. Finally, it is also contemplated that electrically conductive polymers may also be used provided they are bio-compatible or coated with a bio-compatible material.

The present invention permits the construction of a flexible conductive polymer RF ablation electrode that can be used in a wide variety of different tissue environments, including for example, tissues having varying degrees of elasticity and contour.

While the preferred embodiments disclosed in the attached figures disclose an electrode that is generally cylindrical in shape, the present invention also contemplates that the electrode may be formed into various shapes to better fit the contour of the target tissue. In one embodiment, for example, the electrode can be made long enough to strap around and form a noose around the pulmonary veins in epicardial applications. Particularly, electrical conductor 114 that is coupled to the RF energy source may be formed into a desired shape and then the flexible conductive polymer layer may be formed over the conductive element in the preferred shape. For example, the electrode may be shaped like a spatula for certain applications, including for example, minimally invasive sub-xyphoid epicardial applications, where the spatula shape will permit easy placement and navigation in the pericardial sac. Because the conductive polymers used herein are flexible materials, they can be used to form electrodes having a great variety of shapes, including a spatula.

Alternatively, the electrically conductive element that is coupled to the RF energy source (for example, 111, 121, 131, 141, 151, 161 and 171) may be formed using shape-memory retaining material, such as Nitinol, which would permit the electrode to be fitted to specific preset geometries, such as the ostium of a pulmonary vein, such that the electrode is shaped to provide a desired contact pressure pattern on the tissue due to the deformation of the wire when pressed against the tissue.

Similarly, while the reference to insulative shaft (for example, 133, 143, 153, 163, and 173) is generally used in connection with a generally cylindrical member, it is contemplated by the present invention that the insulative shaft could be in a geometric shape other than a cylinder, including, for example, a noose, a spatula, or the shape of the ostium of a pulmonary vein. For purposes of this application, the term "insulative shaft" is intended to encompass shapes in addition to a cylindrical shaft.

Whenever it is desired that the conductive element that is coupled to the RF energy source be formed in the shape of a helix, such as is the case with elements 121, 131, 161 and 171, the coil may be chosen to be of a specific stiffness (that is, having a characteristic spring constant) that would allow the coil to exert a desired amount of pressure when the electrode bends or deflects upon contact with the tissue. One of skill in the art would understand that the degree of desired contact pressure would depend in part upon the elastic property of the tissue being contacted with the electrode. For example, the atrial wall may require less contact pressure than the ventricular wall. Thus, electrodes of varying stiffness can be designed for application in different tissues and different regions of the heart.

In some embodiments, for example, as depicted in FIGS. 4, 5 and 6, the conductive element may be mounted on an insulative shaft. The conductive element can be shaped in any number of ways, including for example, a coil, mesh, coating or wrap. The insulative shaft provides additional mechanical support in applications that require greater amounts of axial force and torque. The insulative shaft may be made of any electrically insulative material, including, for example, polyurethane. Preferably, the insulative shaft is made of a biocompatible, electrically insulative material.

Generally, flexibility is a very desirable characteristic in a catheter. Some applications, however, may require relatively more or less flexibility. Thus, it is contemplated that the same structural design may be used to produce ablation devices of varying flexibility, for example by varying the materials employed in constructing the ablation device.

In other embodiments, for example, as depicted in FIGS. 7A and 8A, the conductive element is mounted on an electrically insulative, thermally conductive shaft. The thermally conductive shaft may improve the cooling of the electrode and the electrode-tissue interface temperature during ablation by thermally conducting the heat from the interface to the ambient flowing blood in endocardial applications. In addition, the thermally conductive shaft can be instrumented with thermal sensors (for example, as depicted in FIGS. 7 and 8) that can be used for temperature controlled RF ablation. The thermally conductive shaft may be made of any electrically insulative, thermally conductive material, including, for example, CoolPoly® thermally conductive, electrically insulative plastic. Preferably, the thermally conductive shaft is made of a biocompatible, thermally conductive, electrically insulative material.

In yet another embodiment, for example, as depicted in FIG. 9A, the cooling efficiency of the ablation electrode can be enhanced by mounting a heat sink 175 at the proximal end of the active electrode 170. The heat sink comprises a material with high thermal conductivity. The use of a heat sink may be particularly useful for small electrodes (typically around 10 mm or less), or for sectioned electrodes that may give rise to hot spots. The heat sink may be made of any electrically insulative, thermally conductive material, including, for example, thermally conductive polyurethane (e.g., polyurethane with thermally conductive ceramic powder embedded therein), diamond, aluminum nitride, boron nitride, silicone, thermal epoxy and thermally conductive, electrically insulative plastics. Preferably, the thermally conductive shaft is made of a biocompatible, thermally conductive, electrically insulative material.

In yet another embodiment, the electrically insulative member may contain one or more passageways for carrying cooling fluids (e.g., saline solution) to the distal end of the electrode. Alternatively, one or more of the passageways may be further defined by a cooling tube made of the same material as, or a material different from, the insulative member. Of course, it is contemplated that the cooling tube and the electrically insulative member may be one in the same (that is, the electrically insulative member itself may define the fluid passageway). If a cooling tube is used in addition to the passageway, the portion of the cooling tube that is located within the catheter shaft is preferably thermally and electrically insulative, while the portion of the cooling tube that is located within the electrode is preferably thermally conductive. The thermally insulative tube inside the catheter shaft is to minimize the degree to which the cooling fluid is heated to body temperature as the result of thermal conduction through the catheter shaft wall as the fluid travels from the outside fluid source through the catheter shaft and to the electrode. The thermally conductive tube inside the electrode, on the other hand, is intended to cool the electrode and the electrode-tissue interface during ablation by thermally conducting the heat from the interface to the flowing fluid inside the tube.

In yet another embodiment, the electrically insulative member may contain one or more passageways for carrying cooling fluids to the actual electrode-tissue interface. The passageways include an inlet to the electrode, and at least one outlet, such as a fluid efflux hole at the distal end of the electrode. Moreover, one or more thermal sensors may be placed in or near the fluid passageway, for example, to measure the temperature of the coolant at the inlet and/or at the outlet. The temperature difference between the inlet and outlet during ablation could be used to monitor the efficacy of the electrode-tissue interface cooling and also to perform temperature-controlled ablation. One or more of the passageways may alternatively be further defined by a cooling tube, which may be made of the same material as, or a material different from, the insulative member, and which, in some embodiments, may be at least partially defined by the insulative member. If a cooling tube is used in addition to the passageway, the portion of the cooling tube that is located within the catheter shaft is preferably thermally insulative, while the portion of the cooling tube that is located within the electrode is preferably thermally and electrically conductive. The thermally insulative tube inside the catheter shaft is to minimize the degree to which the cooling fluid is heated to body temperature as the result of thermal conduction through the catheter shaft wall as the fluid travels from the outside fluid source through the catheter shaft and to the electrode. The thermally conductive tube inside the electrode, on the other hand, is intended to cool the electrode and the electrode-tissue interface during ablation by thermally conducting the heat from the interface to the flowing fluid inside the tube.

Figure 10:
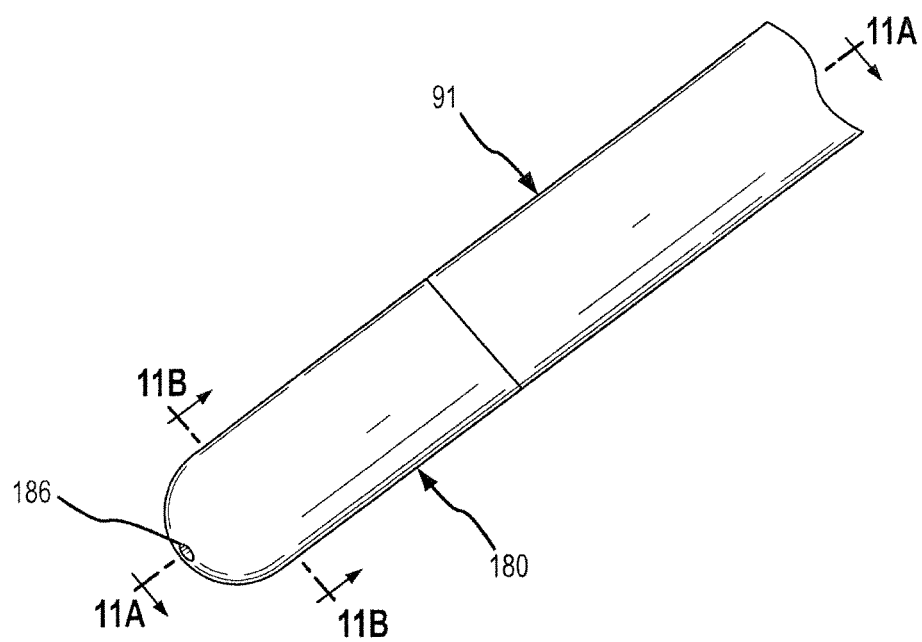
FIG. 10 is a side view of another preferred embodiment of the invention in which the catheter includes a coolant efflux hole.

FIG. 10 illustrates a specific preferred embodiment for the invention of the present application. Electrode 180 extends from a catheter shaft 91 and is connected to an RF energy source (not shown). Electrode 180 further comprises coolant efflux hole 186 that permits the coolant flowing through the core of the catheter from stagnating (and thus heating) inside the catheter. The efflux hole helps to ensure that a fresh supply of coolant is available to keep the working portion of the catheter cool. One of ordinary skill will appreciate that efflux hole 186 could be utilized with any of the preceding embodiments.

It is contemplated that one or more fluid efflux holes may be provided to permit the coolant to exit the electrode. For example, electrode 180 may include a single coolant efflux hole 186 at its distal end as illustrated in FIG. 10. Alternatively, multiple fluid efflux holes may be arranged along electrode 180, for example along its length and/or around its circumference. It may also be desirable to include one or more fluid efflux holes at the junction between electrode 180 and catheter shaft 91.

An irrigated electrode as described above advantageously enhances cooling of both the electrode and the tissue being treated. The coolant flowing through the fluid passageways and out the efflux holes cools the electrode first, and then cools the adjacent tissue by thermal conduction. The flexibility of the irrigated electrode permits the electrode to more closely conform to the tissue surface. This conformance increases the contact area between the electrode and the tissue being treated, which in turn enhances conductive heat transfer from and cooling of the tissue.

Figure 11A:
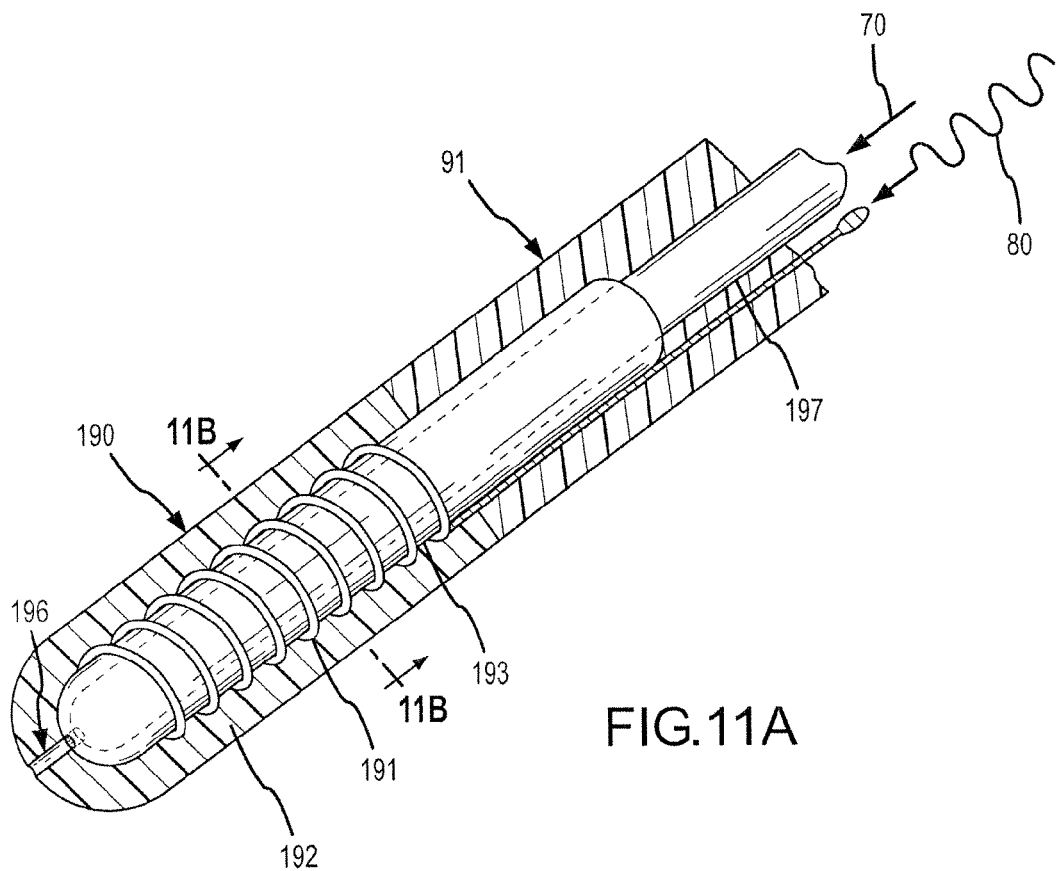
FIGS. 11A and 11B are cross-sectional views of a modified version of the embodiment of FIGS. 5A and 5B including a fluid efflux hole.
Figure 11B:
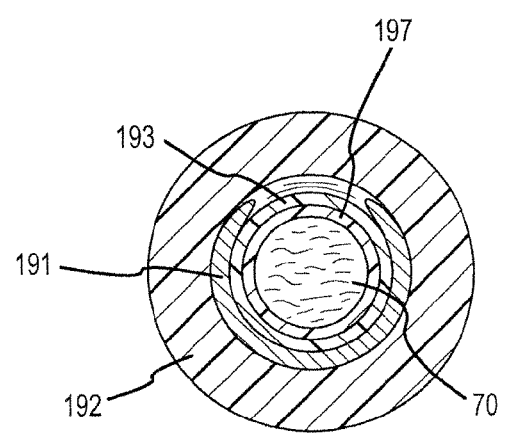

FIGS. 11A and 11B illustrate another preferred embodiment. More particularly, FIGS. 11A and 11B illustrate a modification to the embodiment of FIG. 5 in which efflux hole 196 has been added. Electrode 190 extends from a catheter shaft 91 and is connected to an RF energy source (e.g., RF current source 80). Electrode 190 generally includes: flexible inner conductive coil 191 in the shape of a helix; an outer flexible conductive polymer substrate layer 192; a thermally conductive, electrically insulative flexible tube 193 located partially within the helix of the flexible inner conductive coil 191; and a coolant efflux hole 196. Note that a thermally insulative tube 197 is used in at least a portion of the catheter shaft 91 to help reduce the likelihood of cooling fluid 70 (e.g., saline solution) being heated to body temperature. In this embodiment, note that thermally conductive, electrically insulative flexible tube 193 also forms the thermally conductive, electrically insulative, flexible shaft which is present in other embodiments.

Figure 12A:
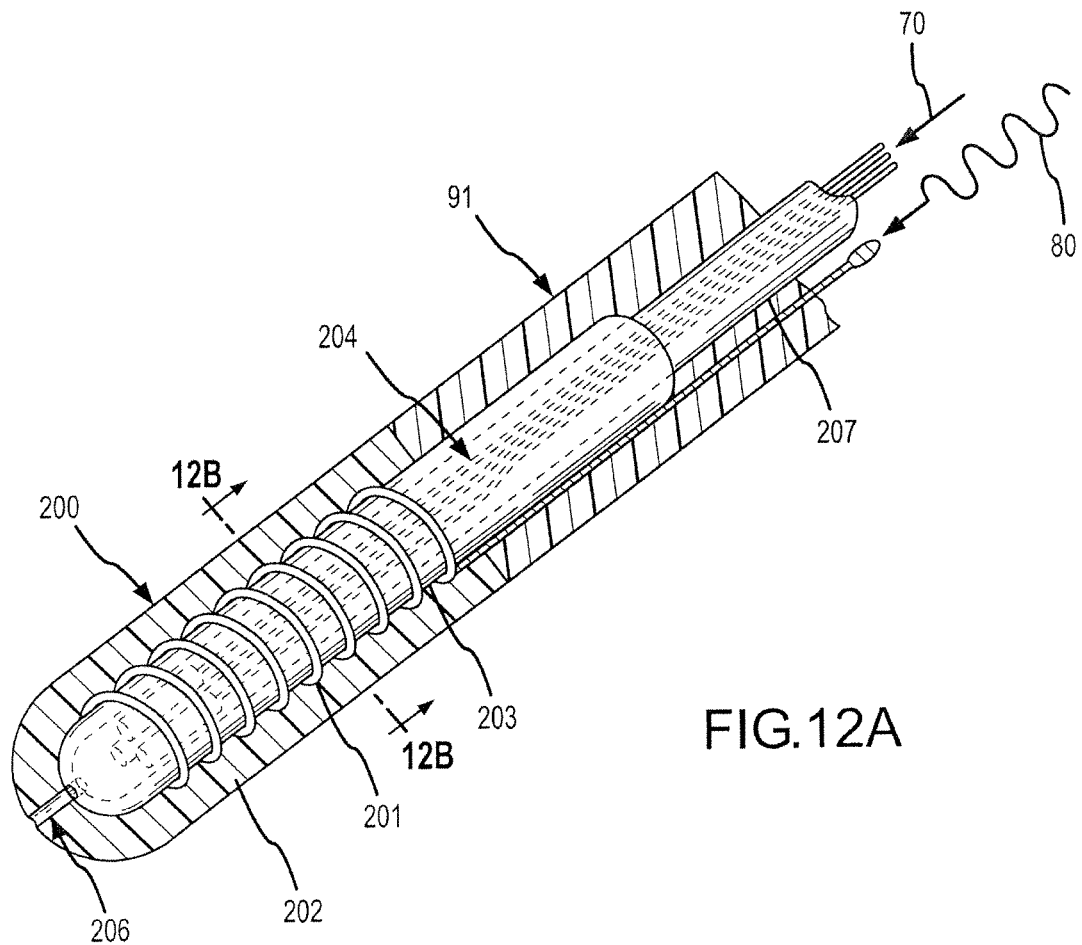
FIGS. 12A and 12B are cross-sectional views of a modified version of the embodiment of FIG. 11A with thermal sensing.
Figure 12B:
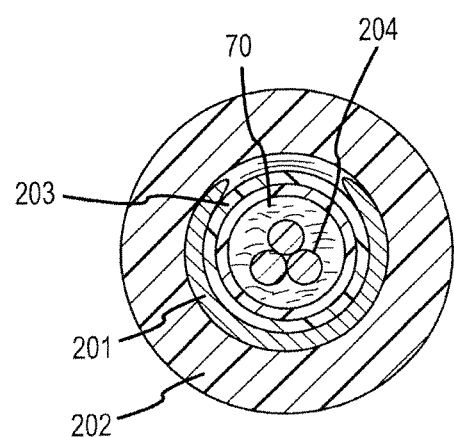

FIGS. 12A and 12B illustrate another preferred embodiment. More particularly, FIGS. 12A and 12B represent a modified version of the embodiment of FIG. 11. Electrode 200 extends from a catheter shaft 91 and is connected to an RF energy source (e.g., RF current source 80). Electrode 200 generally includes: flexible inner conductive coil 201 in the shape of a helix; an outer flexible conductive polymer substrate layer 202; a thermally conductive, electrically insulative flexible tube 203 located partially within the helix of the flexible inner conductive coil 201; a coolant efflux hole 206; and a plurality of thermal sensors 204 located within the thermally conductive, electrically insulative, flexible tube 203 to measure temperatures at various locations therein. Note that a thermally insulative tube 207 is used in at least a portion of the catheter shaft 91 to help reduce the likelihood of cooling fluid 70 being heated to body temperature. In this embodiment, note that thermally conductive, electrically insulative flexible tube 203 also forms the thermally conductive, electrically insulative, flexible shaft which is present in other embodiments.

Figure 13:
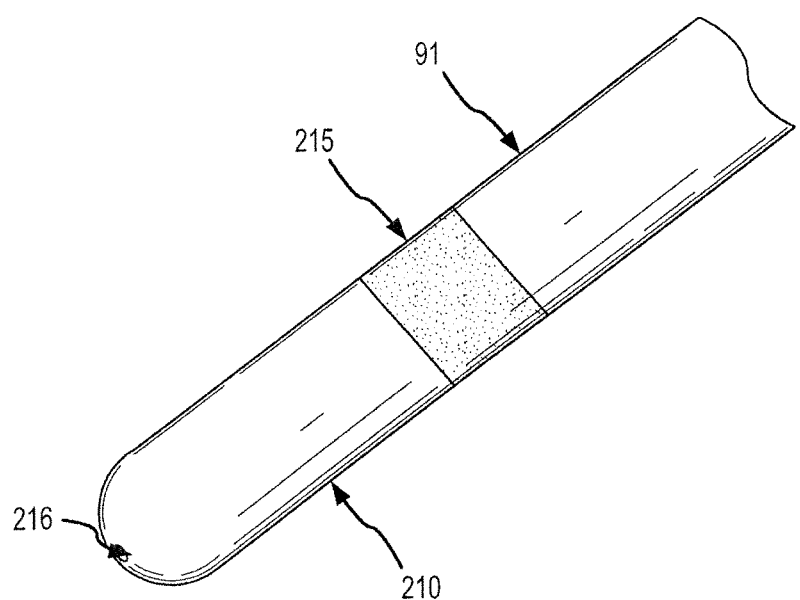
FIG. 13 is a side view of an embodiment that is a modified version of the embodiment of FIG. 10 with a heat sink.

FIG. 13 illustrates yet another preferred embodiment for the invention of the present application. More particularly, FIG. 13 is a modification of the embodiment of FIG. 10. Electrode 210 extends from a catheter shaft 91 and is connected to an RF energy source (not shown). Electrode 210 also includes a heat sink 215 at the proximal end of the electrode and a coolant efflux hole 216 at the distal end of the electrode.

Figure 14A:
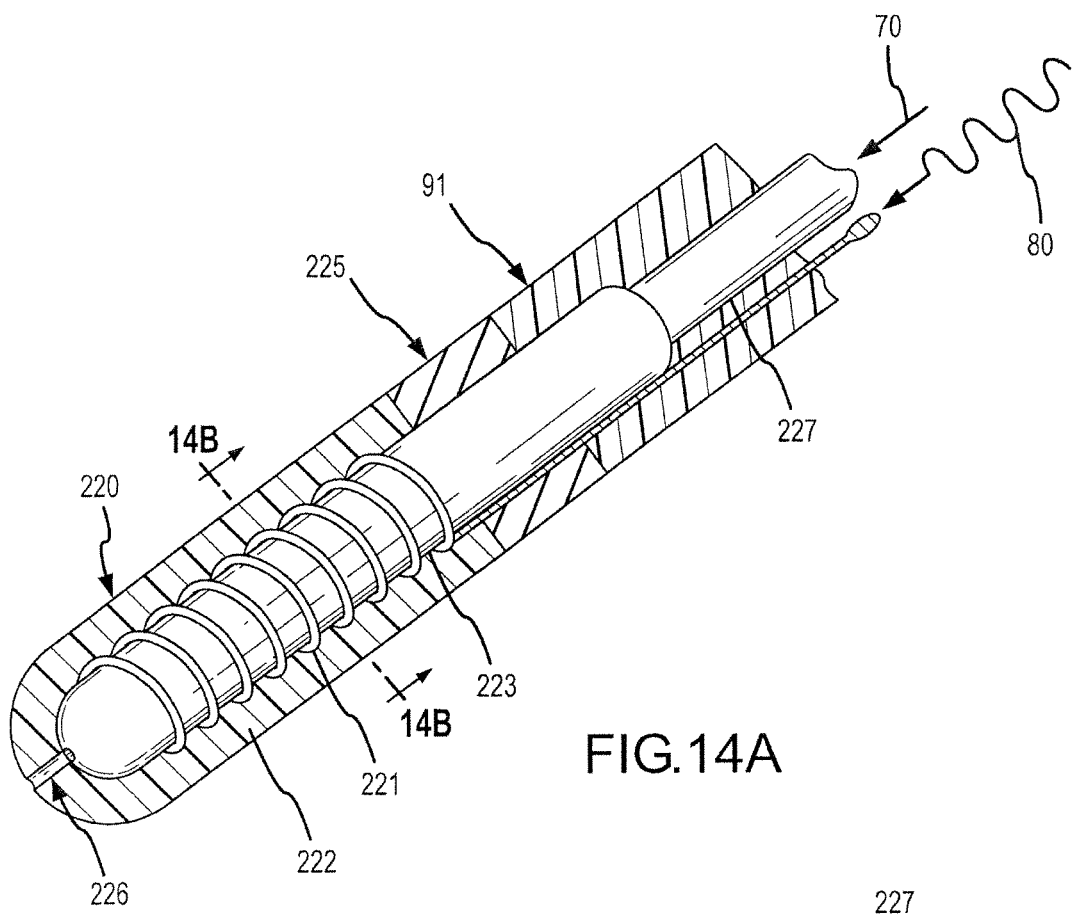
FIGS. 14A and 14B are cross-sectional views of a modification of the embodiment of FIG. 11 with a heat sink.
Figure 14B:
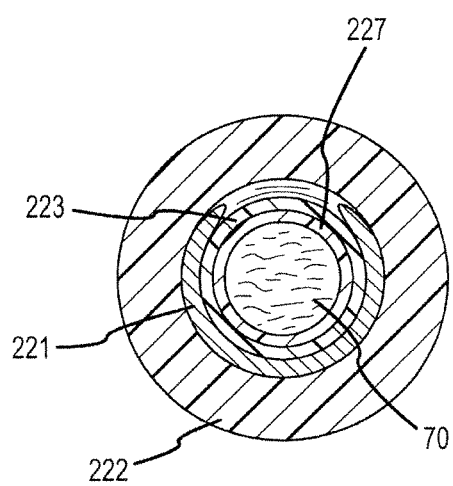

FIGS. 14A and 14B illustrate yet another preferred embodiment. More particularly, FIGS. 14A and 14B represent a modification of the embodiment of FIG. 11. Electrode 220 extends from a catheter shaft 91 and is connected to an RF energy source (e.g., RF current source 80). Electrode 220 generally includes: flexible inner conductive coil 221 in the shape of a helix; an outer flexible conductive polymer substrate layer 222; a thermally conductive, electrically insulative flexible tube 223 located partially within the helix of the flexible inner conductive coil 221; a coolant efflux hole 226; and a heat sink 225 thermally coupled to flexible tube 223. Note that a thermally insulative tube 227 is used in at least a portion of the catheter shaft 91 to help reduce the likelihood of cooling fluid 70 being heated to body temperature. In this embodiment, note that thermally conductive, electrically insulative flexible tube 223 also forms the thermally conductive, electrically insulative, flexible shaft which is present in other embodiments.

Figure 15A:
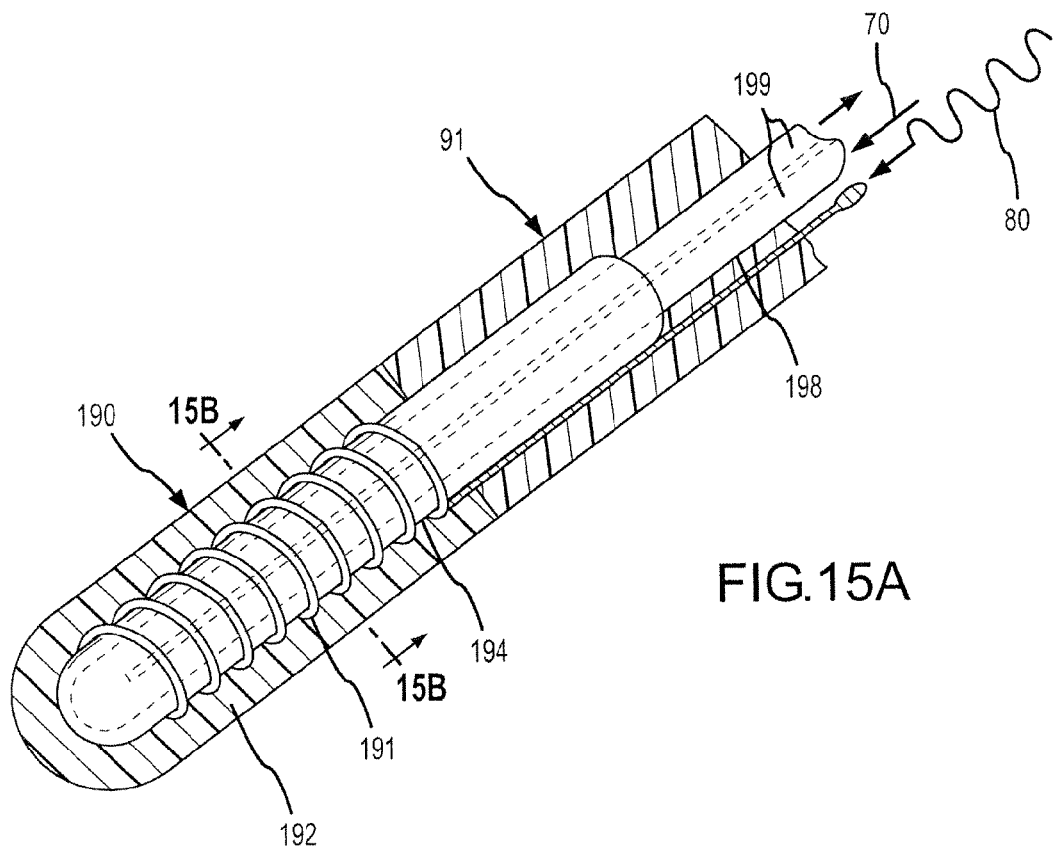
FIGS. 15A and 15B are cross-sectional views of yet another embodiment of the present invention.
Figure 15B:
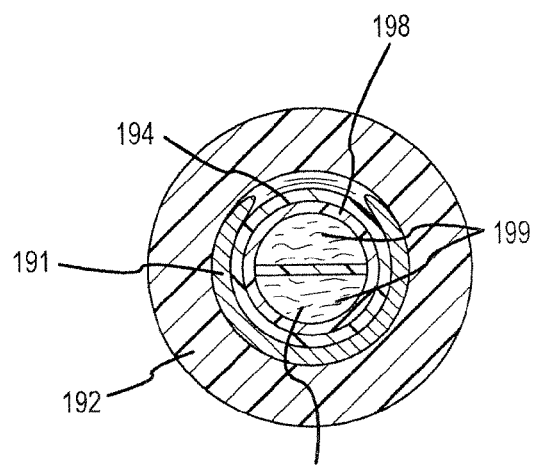

FIGS. 15A and 15B illustrate another preferred embodiment. More particularly, FIGS. 15A and 15B illustrate a preferred embodiment in which a closed loop cooling system has been added. Electrode 190 extends from a catheter shaft 91 and is connected to an RF energy source (e.g., RF current source 80). Electrode 190 generally includes: flexible inner conductive coil 191 in the shape of a helix; an outer flexible conductive polymer substrate layer 192; a thermally conductive flexible shaft 198 located partially within the helix of the flexible inner conductive coil 191; and closed loop cooling passageway 199 located within the flexible shaft 198. Note that a thermally conductive, electrically insulative sleeve 194 may optionally be located between the flexible shaft 198 and inner conductive coil 191. It is contemplated that sleeve 194 may be eliminated, in which case the inner conductive coil 191 may be thermally coupled directly to flexible shaft 198 and closed loop cooling passageway 199. In this embodiment, thermally conductive flexible shaft 198 and closed loop cooling passageway 199 form a closed loop cooling system in which a cooling fluid 70 (e.g., saline) may flow through passageway 199 to cool the distal tip of the catheter during ablation.

In an optional embodiment, any of the electrode designs above may be combined with a processor that monitors the RF current that is being delivered by the RF power source 80. In a preferred embodiment, a computer processor or a microcontroller (not shown) will monitor the maximum current being delivered and use this information to help control the ablation process. Using this information, the computer processor or microcontroller may decrease or increase the power level of the RF power source. By way of example only, the computer processor or microcontroller may be used to limit the total amount of RF energy that is delivered to a certain tissue area. Depending on the nature of the tissue, the power level may be increased to improve lesion creation.

The RF source to be used with the present invention is preferably within the radio frequency range of 200-800 kHz, and more preferably with 250 kHz-550 kHz. The source is preferably capable of delivering up to 150 Watts of electrical power.

The embodiments above may be manufactured in a variety of ways. One such method involves forming an electrode assembly as follows. An electrically insulative shaft may be formed using known electrically insulative materials (which may be thermally conductive or thermally insulative). The shaft is preferably formed of flexible materials. An electrically conductive element for conducting RF energy may be formed on at least a portion of the electrically insulative shaft. In accordance with the teachings above, the conductive element is preferably flexible. A layer of flexible conductive polymer may be formed over at least a portion of the conductive element. In accordance with the teachings above, the electrode assembly may be optionally coated with one or more conductive layers, which are preferably flexible. Preferably, the optional layers are made of a biocompatible, electrically conductive material.

An alternative way to manufacture an electrode assembly of the present invention is as follows. An electrically conductive flexible shaft may be formed using known electrically insulative materials. A layer of flexible conductive polymer may be formed over at least a portion of the conductive shaft. In accordance with the teachings above, the electrode assembly may be optionally coated with one or more flexible conductive layers. Preferably, the optional layers are made of a biocompatible, electrically conductive material.

The electrode assemblies above may also be formed with a fluid lumen and/or one or more fluid efflux holes to permit a cooling fluid to be delivered through the electrode and/or to the tissue during ablation. The assemblies may also be manufactured to include one or more thermal sensors using techniques that are applicable to other known catheter devices.

It is contemplated that each of the embodiments discussed above may optionally be used in connection with one or more electrically-conductive outer coverings. Preferably, the outer covering is electrically conductive, such as a flexible wire mesh, a conductive fabric, a conductive polymer layer (which can be porous or nonporous), or a metal coating. The outer covering may be used to not only increase the mechanical integrity, but to enhance the device's ability to assess the tissue contact (for example, when measuring electrical characteristics using a reference electrode connected to the target tissue or when using the flexible conductive polymer electrode to measure phase angles). In some cases, the outer covering may be made using a biocompatible material in order to help make the overall assembly biocompatible. Preferably the outer covering is flexible.

It is also contemplated that each of the embodiments discussed above may also incorporate one or more electromechanical contact sensors, such as piezoelectric contact sensors, strain gauges, or fiber optic contact sensors. This is described in further detail in U.S. application Ser. No. 11/963,321, filed Dec. 21, 2007, which is expressly incorporated by reference as though fully set forth herein.

Figure 16A:
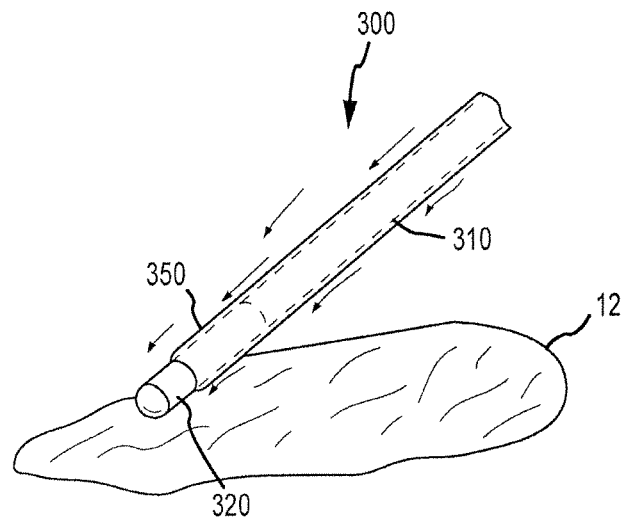
FIGS. 16A and 16B are perspective views of another embodiment of the present invention, illustrating how the present invention may be used to ablate tissue.
Figure 16B:
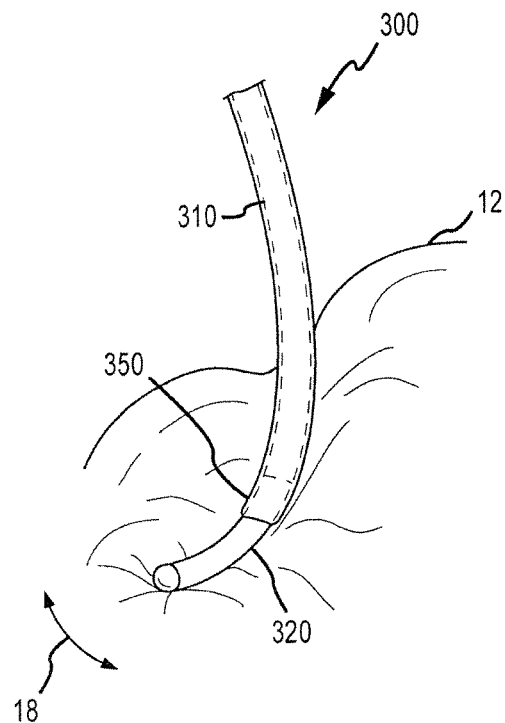

FIGS. 16A and 16B illustrate another preferred embodiment of a catheter having an adjustable-length flexible polymer electrode. A catheter 300 generally includes a catheter shaft 310, an adjustable-length flexible polymer electrode tip 320 that extends distally from the catheter shaft 310, and an insulative sheath 350 that surrounds the catheter shaft 310 and at least a portion of the adjustable-length flexible polymer electrode tip 320. The catheter 300 is flexible such that when it comes into contact with tissue 12, the adjustable-length flexible polymer electrode tip 320 is deflected in direction 18 as illustrated in FIG. 16B, thereby increasing the contact surface between the electrode tip 320 and the tissue 12. As will be explained more fully below, the adjustable-length flexible polymer electrode tip 320 and the insulative sheath 350 are movable with respect to one another to expose more or less of the electrode tip 320 and thus permit the formation of ablation lesions of various types and sizes during a single treatment session.

Figure 17:
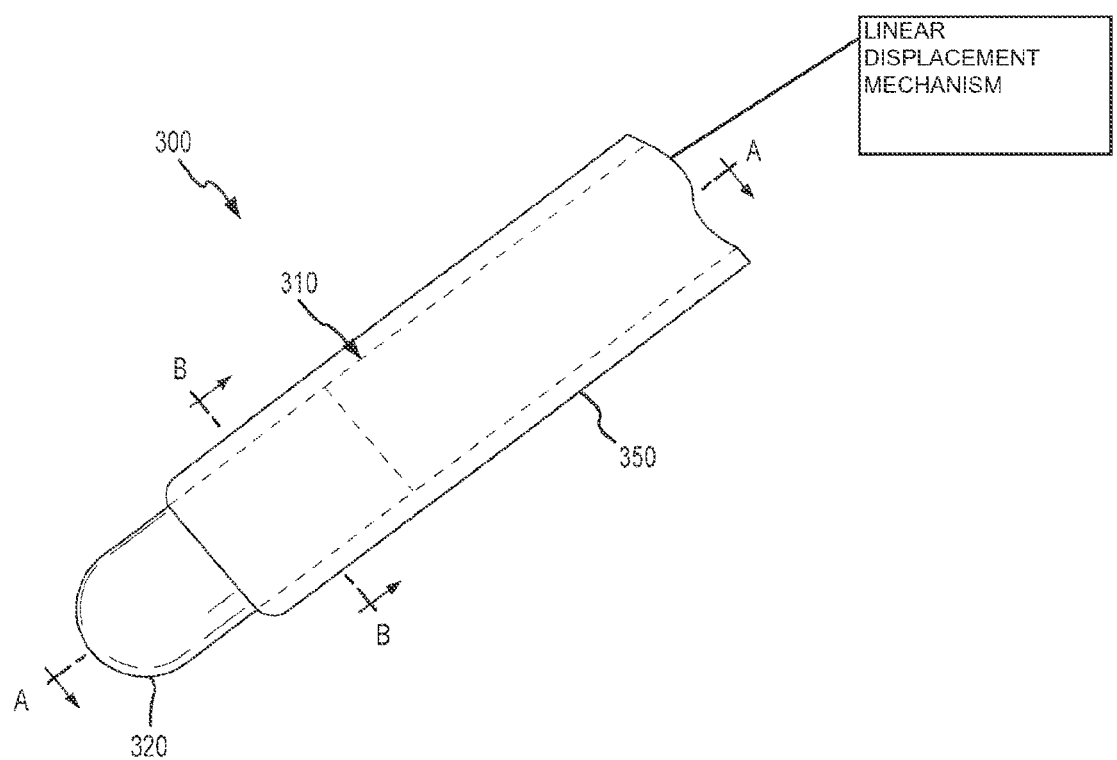
FIG. 17 is a side view drawing of an exemplary catheter having an adjustable-length flexible polymer electrode.
Figure 19A:
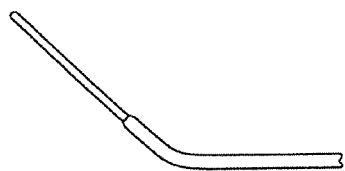
FIGS. 19A-D illustrate various lengths of an adjustable-length flexible polymer electrode according to one embodiment of the invention.
Figure 19B:
Figure 19C:
Figure 19D:

FIG. 17 is a close-up of the sample embodiment depicted in FIGS. 16A and 16B. FIG. 2 illustrates cross-sectional reference lines A-A and B-B, which will be used to illustrate preferred embodiments of the present invention.

FIGS. 18A and 18B illustrate a preferred embodiment of the present invention, revealing two cross sectional drawings taken along the reference lines of A-A and B-B as labeled in FIG. 17. In this preferred embodiment, the catheter 300 includes a catheter shaft 310, an adjustable-length flexible polymer electrode tip 320 (which will also be referred to herein as the electrode tip 320) that extends distally from the catheter shaft 310, and an insulative sheath 350. A proximal end 325 of the electrode tip 320 may overlap with a distal end 315 of the catheter shaft 310, as shown in FIG. 17. Alternatively, the proximal end 325 of the electrode tip 320 and the distal end 315 of the catheter shaft may abut one another. The catheter shaft 310 may be either conductive or non-conductive, and preferably, catheter shaft 310 is non-conductive.

As depicted in FIGS. 18A and 18B, the adjustable-length flexible polymer electrode tip 320 includes a flexible inner conductive element 370 and an outer conductive polymer substrate layer 360, which is mechanically and electrically coupled to the flexible inner conductive element 370. The flexible inner conductive element 370 may include a flexible inner conductive coil 330 in the shape of a helix that surrounds a flexible shaft 340 as shown in FIG. 18A. One of skill in the art will appreciate, however, that the flexible inner conductive element 370 may take other forms. For example, the flexible inner conductive element 370 may include an inner conductive core 111 (see FIGS. 3A and 3B), an inner conductive coil 121 (see FIGS. 4A and 4B), an inner conductive mesh sheath 141 (see FIGS. 6A and 6B), or an inner conductive coating or wrap 151 (see FIGS. 7A and 7B). The flexible shaft 340 is preferably an electrically insulative shaft, but may be electrically conductive without departing from the spirit and scope of the present invention. Moreover, the flexible shaft 340 may be thermally conductive. The flexible shaft 340 may include a flattened distal end as shown in FIG. 18A. Alternatively, the flexible shaft 340 may include a rounded distal end.

The flexible inner conductive coil 330 is preferably connected to an electrical conductor 335, which may be connected to an RF generator (e.g., RF current source 345). In use, in this preferred embodiment, the electrode tip 320 ablates tissue by delivering energy through the inner conductive coil 330. Preferably, the reference electrode is electrically connected to an electrical ground reference signal.

The insulative sheath 350 extends over at least a portion of the catheter shaft 310 and at least a portion of the adjustable-length flexible polymer electrode tip 320. The insulative sheath 350 is preferably made of a biocompatible electrically insulative material, including, for example, a polymeric material, such as an extruded polytetrafluoroethylene (PTFE) tubing (e.g., Teflon® brand tubing). In one preferred embodiment, the insulative sheath 350 is slidable over the electrode tip 320 and the catheter shaft 310. In another preferred embodiment, the electrode tip 320 and the catheter shaft 310 are slidable within the insulative sheath 350. Of course, as a person of skill in the art will appreciate, the electrode tip 320 (and catheter shaft 310) and insulative sheath 350 may be slidable with respect to each other.

In these embodiments, the length of the electrode tip 320 that is exposed (i.e., the length that is not surrounded by the insulative sheath 350) can be varied. In particular, the insulative sheath 350 and/or the electrode tip 320 may be moved in a proximal and a distal direction to vary the length of the exposed portion of the electrode tip 350. It is advantageous to be able to adjust the length of the exposed portion of the electrode tip 320 in order to create various types and sizes of ablation lesions. In other words, after insertion into a body cavity, the device will be able to create multiple lesions, such as spot lesions and continuous lesions, of multiple sizes during a single treatment session.

As shown in FIGS. 9A-9D, the adjustable-length flexible polymer electrode tip 320 can be adjusted to expose various lengths of the electrode tip 320 distally of the insulative sheath 350. For example, the exposed portion of the electrode tip 320 may have a length of about 0.1 mm to about 100 mm. The device may optionally include a seal between the electrode tip 320 and the insulative sheath 350 to ensure that no fluid leaks between the electrode tip 320 and the insulative sheath 350.

In one preferred embodiment, a linear displacement mechanism (not shown) is mechanically coupled to at least one of the insulative sheath 350 and the electrode tip 320. The linear displacement mechanism may include a push-pull pulley, a screw drive or a rack and pinion mechanism. The linear displacement mechanism preferably includes actuating means in a proximal handle (not shown) or other proximal location of the catheter 300 for actuating the linear displacement mechanism. The actuating means may be driven manually or using electromechanical means such as servo-motors.

A method of ablating tissue will now be described. A catheter 300 having an adjustable-length flexible polymer electrode tip 320 and an insulative sheath 350 surrounding at least a portion of the electrode tip 320 is provided. The catheter 300 is inserted into a body cavity and an exposed portion of the electrode tip 320 is placed against a tissue to be ablated, for example an epicardial surface. The exposed portion of the electrode tip 320 is the portion that is not surrounded by the insulative sheath 350. The electrode tip 320 is energized, for example with RF energy, to create a first lesion having a first length. At least one of the electrode tip 320 and the insulative sheath 350 is adjusted to increase or decrease the length of the exposed portion of the electrode tip 320. A linear displacement mechanism may be used to adjust the electrode tip 320 and/or the insulative sheath 350. After adjusting the length of the exposed portion of the electrode tip 320, the electrode tip 320 is energized a second time to create a second lesion having a second length. The lengths of the first lesion and the second lesion may be between about 0.5 mm and about 50 mm. The first lesion and the second lesion may be spot lesions or continuous lesions. The electrode tip 320 and/or the insulative sheath 350 may be adjusted a third or more times to increase or decrease the length of the exposed portion of the electrode tip 320 as necessary to create additional lesions of different sizes.

Although multiple embodiments of this invention have been described above with a certain degree of particularity, those skilled in the art could make numerous alterations to the disclosed embodiments without departing from the spirit or scope of this invention. For example, one of skill in the art will appreciate that the various principles and features described above may be employed in numerous combinations and permutations in accordance with the spirit and scope of the present invention.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An ablation catheter, comprising:
a flexible elongated shaft;
a flexible electrode coupled to a distal end of the flexible elongated shaft, the flexible electrode comprising
an inner, flexible, electrically-conductive element; and
an outer, flexible, electrically-conductive polymer layer in electrical contact with the inner, flexible, electrically-conductive element;
an electrically insulative sheath surrounding at least a portion of the flexible electrode; and
a linear displacement mechanism capable of adjusting at least one of the electrically insulative sheath and the flexible electrode to vary a length of the flexible electrode exposed at the distal end of the flexible elongated shaft.

2. The ablation catheter of claim 1, wherein the length of the flexible electrode exposed at the distal end of the flexible elongated shaft varies from about 0.1 mm to about 100 mm.

3. The ablation catheter of claim 1, wherein the length of the flexible electrode exposed at the distal end of the flexible elongated shaft varies from about 0.5 mm to about 25 mm.

4. The ablation catheter of claim 1, wherein the linear displacement mechanism comprises a push-pull pulley.

5. The ablation catheter of claim 1, wherein the linear displacement mechanism comprises a screw drive mechanism.

6. The ablation catheter of claim 1, wherein the linear displacement mechanism comprises a rack and pinion mechanism.

7. The ablation catheter of claim 1, wherein the inner electrically conductive element comprises a helical coil.

8. The ablation catheter of claim 1 further comprising a seal between the electrically insulative sheath and the flexible shaft.

9. An adjustable length ablation electrode, comprising:
an inner, flexible, electrically-conductive element;
an outer, flexible, electrically-conductive polymer layer in electrical contact with the inner, flexible, electrically-conductive element; and
an electrically insulative sheath surrounding at least a portion of the outer, flexible, electrically-conductive polymer layer,
wherein the electrically insulative sheath is movable from a first position to a second position, and wherein the electrically insulative sheath exposes a first length of the ablation electrode in the first position and a second length of the ablation electrode in the second position, the second length being greater than the first length.

10. The adjustable length ablation electrode of claim 9, wherein the first length and the second length are each between about 0.1 mm and about 100 mm.

11. The adjustable length ablation electrode of claim 9 further comprising a linear displacement mechanism for moving the electrically insulative sheath between the first position and the second position.

12. The adjustable length ablation electrode of claim 11, wherein the linear displacement mechanism comprises at least one of a push-pull pulley, a screw drive mechanism and a rack and pinion mechanism.

13. The adjustable length ablation electrode of claim 9, wherein the inner electrically conductive element comprises a helical coil.

14. The adjustable length ablation electrode of claim 9 further comprising a seal between the electrically insulative sheath and the outer electrically conductive polymer layer.

15. An ablation catheter, comprising:
a flexible, elongated shaft;
a flexible electrode coupled to a distal end of the flexible, elongated shaft, the flexible electrode comprising an inner, flexible, electrically conductive element and an outer, flexible, electrically conductive polymer layer in electrical contact with the inner, flexible, electrically-conductive element; and
an electrically insulative sheath surrounding at least a portion of the flexible electrode,
wherein the flexible electrode and the electrically insulative sheath are movable with respect to each other to expose more or less of a length of the flexible electrode.

16. The ablation catheter of claim 15, wherein the flexible electrode and the electrically insulative sheath are movable with respect to each other to expose a length of the flexible electrode of between about 0.1 mm and about 100 mm.

17. The ablation catheter of claim 15 further comprising a linear displacement mechanism adapted to move the flexible electrode and the electrically insulative sheath with respect to each other.

18. The ablation catheter of claim 17, wherein the linear displacement mechanism comprises at least one of a push-pull pulley, a screw drive mechanism, and a rack and pinion mechanism.

19. The ablation catheter of claim 15, wherein the inner electrically conductive element comprises a helical coil.

20. The ablation catheter of claim 15 further comprising a seal between the electrically insulative sheath and the flexible electrode.

21. A method for ablating tissue, comprising:
providing an ablation catheter having a flexible elongated shaft; a flexible electrode coupled to a distal end of the flexible elongated shaft, the flexible electrode comprising an inner, flexible, electrically conductive element and an outer, flexible, electrically conductive polymer layer in electrical contact with the inner, flexible, electrically conductive element; and an electrically insulative sheath surrounding at least a portion of the flexible electrode;
placing the exposed portion of the flexible electrode against tissue to be ablated;
energizing the electrode to create a first lesion having a first length;
adjusting at least one of the flexible electrode and the electrically insulative sheath to increase or decrease the length of the exposed portion of the flexible electrode;
energizing the flexible electrode to create a second lesion having a second length.

22. The method of claim 21, wherein the first length and the second length are between about 0.1 mm and about 100 mm.

23. The method of claim 21, wherein the tissue is an epicardial tissue.

24. The method of claim 21, wherein the adjusting step comprises actuating a linear displacement mechanism to adjust at least one of the electrically insulative sheath and the flexible electrode.

25. The method of claim 24, wherein the linear displacement mechanism comprises one of a push-pull pulley, a screw drive mechanism, and a rack and pinion mechanism.

* * * * *